(12) United States Patent
Buchwald et al.

(10) Patent No.: US 6,787,655 B2
(45) Date of Patent: *Sep. 7, 2004

(54) ASYMMETRIC 1,4-REDUCTIONS OF AND 1,4-ADDITIONS TO ENOATES AND RELATED SYSTEMS

(75) Inventors: Stephen L. Buchwald, Newton, MA (US); Daniel H. Appella, Boston, MA (US); Yasunori Moritani, Brookline, MA (US); Ryo Shintani, Cambridge, MA (US); Valdas Jurkauskas, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/272,501

(22) Filed: Oct. 15, 2002

(65) Prior Publication Data

US 2003/0125563 A1 Jul. 3, 2003

Related U.S. Application Data

(63) Continuation of application No. 09/662,430, filed on Sep. 13, 2000, now Pat. No. 6,465,664.
(60) Provisional application No. 60/154,008, filed on Sep. 15, 1999.

(51) Int. Cl.[7] .................... C07D 309/30; C07D 307/33; C07C 69/76; C07C 45/62
(52) U.S. Cl. ...................... 549/273; 549/295; 549/323; 560/8; 568/343; 568/347; 568/376; 568/379; 568/392
(58) Field of Search ................................ 549/273, 295, 549/323; 560/8; 568/343, 347, 376, 379, 392

(56) References Cited

U.S. PATENT DOCUMENTS

| 4,772,755 | A | | 9/1988 | Liotta et al. ................. 568/646 |
| 4,962,214 | A | | 10/1990 | Villacorta et al. ............ 556/33 |
| 5,162,586 | A | | 11/1992 | Villacorta et al. .......... 568/312 |
| 5,440,062 | A | | 8/1995 | Villacorta et al. ............ 556/33 |
| 5,936,127 | A | | 8/1999 | Zhang .......................... 568/12 |
| 6,465,664 | B1 | * | 10/2002 | Buchwald et al. .......... 549/273 |

FOREIGN PATENT DOCUMENTS

| DE | 2 363 051 | 7/1974 |
| JP | 521 339 51 | 11/1977 |
| WO | WO 98/30543 | 7/1998 |
| WO | WO 99/07367 | 2/1999 |
| WO | WO 00/50430 | 8/2000 |

OTHER PUBLICATIONS

Alexakis et al.; "Catatylic Asymmetric Conjugate Addition on Macrocyclic and Acyclic Enones. Synthesis of R–(–)–Muscone", Synlett 11: 1811–1813, (1999).

Alexakis et al.; "New Chiral Ligand for the Asymmetric Conjugate Addition of organocopper Reagent to Enones", J. Am. Chem. Soc. 113:6332–6334, (1991).

Alexakis et al.; "Asymmetric Conjugate Addition of Diethyl Zinc to Enones With Chiral Phosphorus Ligands Derived From TADDOL", Tetrahedron Letters 39: 7869–7872, (1998).

Alexakis et al.; "Asymmetric Conjugate Addition of Diethyl Zinc to Enones with Chiral Phosphine Ligands", Tetrahedron: Asymmetry 8(24): 3987–3990, (1997).

Appella et al.; "Asymmetric Conjugate Reduction of aμ–Unsaturated Esters Using a Chiral Phosphine–Copper Catalyst", J. Am. Chem. Soc. 121: 9473–9474, (1999).

Bennett et al.; "Copper–Catalysed Asymmetric Conjugate Addition of Organometallic Reagents to Linear Enones", Tetrahedron 56: 2847–2855, (2000).

Enders et al.; "Asymmetric Nucleophilic α–amino–acylation with Metalated Chiral Amino Nitriles: Enantioselective Synthesis of 3–substituted 5–amino–4–oxo–esters via asymmetric Michael Addition", J. Chem. Soc., Perkin Trans. 1:1617–1619, (1999).

Frey et al.; "Stereoselective Conjugate Addition Reactions of α–β–Unsaturated tert–Butyl Esters with Aryllithium Reagents", J. Org. Chem. 63: 3120–3124, (1998).

Kanai and Tomioka, "Catalytic Asymmetric Conjugate Addition of Grignard Reagents Mediated by Copper-(I)–Chiral Bidentate Phosphine Complex", Tetrahedron Letters 36(24): 4275–4278, (1995).

Kang et al.; "Examination of Bidentate Thiol Derivatives as Ligands in the Ni–Catalyzed Asymmetric Conjugate Addition of Diethylzinc to Enones", Bull. Korean Chem. Soc. 19(5): 601–603, (1998).

Leutenegger et al.; "Enantioselective Reduction of α,β–Unsaturated Carboxylates with NaBH$_4$ and Catalytic Amounts of Chiral Cobalt Semicorim Complxes", Angew. Chem. Int. Ed. Engl. 28(1):60–61, (1989).

Lipshutz et al.; "A convenient, Efficient Method for Conjugate Reductions Using Catalytic Quantities of Cu (I)", Tetrahedron Letters 39: 4627–4630, (1998).

Massonneau et al.; "Catalytic Asymmetric Syntheses II. Hydrogenation of α,β–Unsaturated Ketones Using Chiral Ruthenium Complexes", Journal of Organometallic Chemistry 327:269–273, (1987).

(List continued on next page.)

Primary Examiner—Ba K. Trinh
(74) Attorney, Agent, or Firm—Dana M. Gordon; Foley Hoag LLP

(57) ABSTRACT

One aspect of the present invention relates to methods for the transition-metal-catalyzed asymmetric 1,4-addition of a nucleophile, e.g., hydride, to cyclic and acyclic enoates and enones. In certain embodiments of the methods of the present invention, the transition metal catalyst consists essentially of copper and an asymmetric bidentate bisphosphine ligand.

20 Claims, 7 Drawing Sheets

OTHER PUBLICATIONS

Nicolas et al.; "Asymmetric 1,4–Addition of Organocuprates to Chiral α,β–Unsaturated N–Acyl–4–Phenyl–2–Oxazolidinones: A New Approach to the Synthesis of Chiral β–Branched Carboxylic Acids", J. Org. Chem. 58: 766–770, (1993).

Pàmies et al.; "Copper–Catalysed Asymmetric Conjugate Addition of Organometallic Reagents to Enones Using S, O–ligands with a Xylofuranose Backbone", Tetrahedron: Asymmetry 11: 871–877, (2000).

Soai et al.; "Enantioselective Conjugate Addition of Diethylzinc to Enones Using Chiral β–Aminoalcohol as Chiral Catalyst or Ligand", Tetrahedron Letters 32(1): 95–96, (Jan. 1, 1991).

Soai et al.; "Asymmetric Synthesis of Optically Active β–Substituted Ketones by Highly Enantioselective Catalytic Conjugate Addition of Dialkylzinc Reagents to Enones Using a Catalyst System of Nickel(II)–Chiral Ligand–Achiral Ligand in Acetonitrile/Toluene", J. Chem. Soc. Chem. Commun., 516–517, (1989).

Stangeland and Sammakia; "New Chiral Ligands for the Asymmetric Copper Catalyzed Conjugate Addition of Grignard Reagents to Enones", Tetrahedron 53 (48): 16503–16510, (1997).

Tomioka et al.; "Enantioselective Conjugate Addition Reaction Mediated by Chiral Ligands", Chemistry Letters, pp. 329–332, (1985).

* cited by examiner

Kinetic Resolution Results

| R | R' | Temp., °C | Catalyst, mol % | ee (%) [a] | C (%) [b] | S |
|---|---|---|---|---|---|---|
| -CH₂CH₂Ph | CH₃- | 0 | 5 | 72.0 | 52.0 | 11 |
| -CH₂CH₂Ph | C₄H₉- | -78 | 5 | 46.0 | 35.0 | 20 |
| -CH₂CH₂Ph | (CH₃)₂CH- | 0 | 5 | 32.9 | 26.5 | 30 |
| -CH₂CH₂Ph | (CH₃)₃C- | 0 | 5 | 40.6 | 30.1 | 51 |
| -CH₂CH₂Ph | C₆H₅- | 0 | 5 | 32.6 | 26.6 | 26 |
| -CH₂(CH₂)₂CH₂OCH₂Ph | (CH₃)₃C- | 0 | 5 | 20.8 | 17.3 | 429 |
| -CH₂(CH₂)₂CH₂OCH₂Ph | CH₂=CHCH₂CH₂- | -78 | 10 | 60.6 | 42.3 | 22 | a - ee of (2), b - conversion of (1)

Figure 6

Asymmetric Conjugate Reduction with (S)-TolBINAP, CuCl, NaOt-Bu, and PMHS.

| entry | substrate | product | time (h) | yield (%) | ee (%) |
|---|---|---|---|---|---|
| 1 | 1a | 2a | 20 | 21 | |
| 2 | 1b | 2b | 72 | 60 | 88 |
| 3 | 1c | 2c | 49 | 59 | 83 |
| 4 | 1d | 2d | 40 | 53 | 75 |
| 5 | 1e | 2e | 24 | 64 | 80 |
| 6 | 1f | 2f | 37 | 49 | 75 |
| 7 | 1g | 2g | 16 | 30 | 52 |

Reactions were undertaken at 0.25 M of substrate with 4 eq of PMHS, 5 mol% CuCl, 5 mol% NaOt-Bu, and 10 mol% of (s)-p-tol-BINAP at room temperature.

Figure 7

Asymmetric Conjugate Reduction with Chiral Ligand, CuCl, NaO*t*-Bu, and PMHS.

| entry | substrate | product | ligand | Condition | time (h) | yield (%) | ee (%) |
|---|---|---|---|---|---|---|---|
| 1 | 1e | 2e | (s)-tol-BINAP | A | 24 | 64 | 80 |
| 2 | | | (s)-tol-BINAP | B | 54 | 91 | 69 |
| 3 | | | (s)-BINAP | A | 37 | 48 | 69 |
| 4 | 1f | 2f | (s)-tol-BINAP | A | 37 | 49 | 75 |
| 5 | | | (s)-tol-BINAP | B | 46 | 60 | 76 |
| 6 | | | (s)-BINAP | A | 79 | 32 | 74 |
| 7 | 1g | 2g | (s)-tol-BINAP | A | 16 | 30 | 52 |
| 8 | | | (s)-BINAP | A | 25 | 35 | 61 |
| 9 | | | (-)-NORPHOS | A | 70 | 20 | 2 |
| 10 | | | Pfaltz ligand | A | 45 | N.R. | — |
| 11 | | | (-)-BIPHEMP | A | 49 | 36 [a] | 83 |

Condition A: 0.25 M of substrate with 4 eq of PMHS, 5 mol% CuCl, 5 mol% NaO*t*-Bu, and 10 mol% of Chiral Ligand at room temperature.
Condition B: 0.25 M of substrate with 4 eq of PMHS, 10 mol% CuCl, 10 mol% NaO*t*-Bu, and 10 mol% of Chiral Ligand at room temperature.
a) Conversion: 73%

*Chiral Ligands*

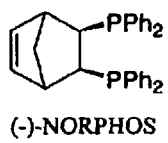
(-)-NORPHOS

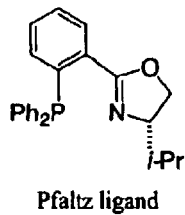
Pfaltz ligand

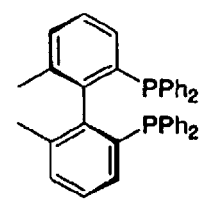
(-)-BIPHEMP

ASYMMETRIC 1,4-REDUCTIONS OF AND 1,4-ADDITIONS TO ENOATES AND RELATED SYSTEMS

RELATED APPLICATIONS

This application is a continuation of U.S. patent application Ser. No. 09/662,430, filed Sep. 13, 2000, now U.S. Pat. No. 6,465,664; which claims the benefit of priority to U.S. Provisional Patent Application serial No. 60/154,008, filed Sep. 15, 1999.

GOVERNMENT SUPPORT

This invention was made with support from the National Institutes of Health (GM 46059). The government, therefore, has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. The advantages of enantiomerically pure compounds (reviewed in, e.g., Stinson, S. C., *Chem Eng News*, Sep. 28, 1992, pp. 46–79) include fewer side effects and greater potency in many cases.

Traditional methods of organic synthesis have often been optimized for the production of racemic materials. The production of enantiomerically pure material has historically been achieved in one of two ways: the use of enantiomerically pure starting materials derived from natural sources (the so-called "chiral pool"); or the resolution of racemic mixtures by classical techniques. Each of these methods has serious drawbacks, however. The chiral pool is limited to compounds found in nature, so only certain structures and absolute configurations are readily available. Resolution of racemates often requires the use of resolving agents; this process may be inconvenient and is certain to be time-consuming. Furthermore, resolution often means that the undesired enantiomer is discarded, thereby wasting half of the material.

Currently, few catalysts are available that can reduce carbon-carbon double bonds to generate asymmetric products wherein the products comprise a stereocenter β to a carbonyl group and are produced in high enantiomeric excess (ee). In this area, asymmetric conjugate additions of nucleophiles to α,β-unsaturated ketones have been investigated; however, the best catalysts for these reactions work well for only a limited number of substrates and nucleophiles. In certain limited cases, asymmetric hydrogenation catalysts can provide access to products with stereocenters β to carbonyls. Asymmetric conjugate reduction of an α,β-unsaturated carbonyl portion of a molecule is also capable of generating a stereocenter β to a carbonyl. Despite the availability of catalysts for conjugate reductions, only Pfaltz's chiral semicorrin cobalt system is an effective catalyst for asymmetric conjugate reductions. In this system, sodium borohydride is used as the stoichiometric reducing agent.

The ability to effect asymmetric 1,4-reduction of and asymmetric 1,4-addition to enoates and the like, in good yield, with good enantiomeric excess, and under mild reaction conditions, would constitute a highly desirable addition to the palette of synthetic transformations available to research and process chemists in both academic and industrial settings. The ability to realize these goals utilizing asymmetric catalysis, e.g., asymmetric transition metal catalysts, is particularly appealing. Furthermore, the ability to achieve these transformations without the need to resort to the use of metal hydrides is also highly desirable.

SUMMARY OF THE INVENTION

One aspect of the present invention relates to the transition metal catalyzed asymmetric 1,4-reduction of enoates and related systems, e.g., enones and acrylonitriles. Another aspect of the present invention relates to the transition metal catalyzed asymmetric 1,4-addition of nucleophiles to enoates and related systems, e.g., enones and acrylonitriles. In certain embodiments of the present invention, the asymmetric 1,4-reductions and 1,4-additions rely upon a transition metal catalyst consisting essentially of copper and an asymmetric bidentate ligand.

For example, highly enantioselective conjugate reductions of α,β-unsaturated esters were achieved by combining catalytic amounts of CuCl, NaOt-Bu, and (S)-p-Tol-BINAP with 4 equivalents of PMHS relative to the substrate. These reductions proceeded at room temperature to give products in high yields and with enantiomeric excesses of 80–92%.

BRIEF DESCRIPTION OF THE FIGURE

FIG. 6 tabulates the results of seven asymmetric 1,4-reductions of cyclic enoates, using PMHS, (S)-p-tol-BINAP, 10 mol % sodium tert-butoxide, and 5 mol % copper(I) chloride.

FIG. 7 tabulates, as a function of the asymmetric ligand used, the results of eleven asymmetric 1,4-reductions of cyclic enoates, using PMHS, sodium tert-butoxide, and copper(I) chloride.

DETAILED DESCRIPTION OF THE INVENTION

Figure 1:
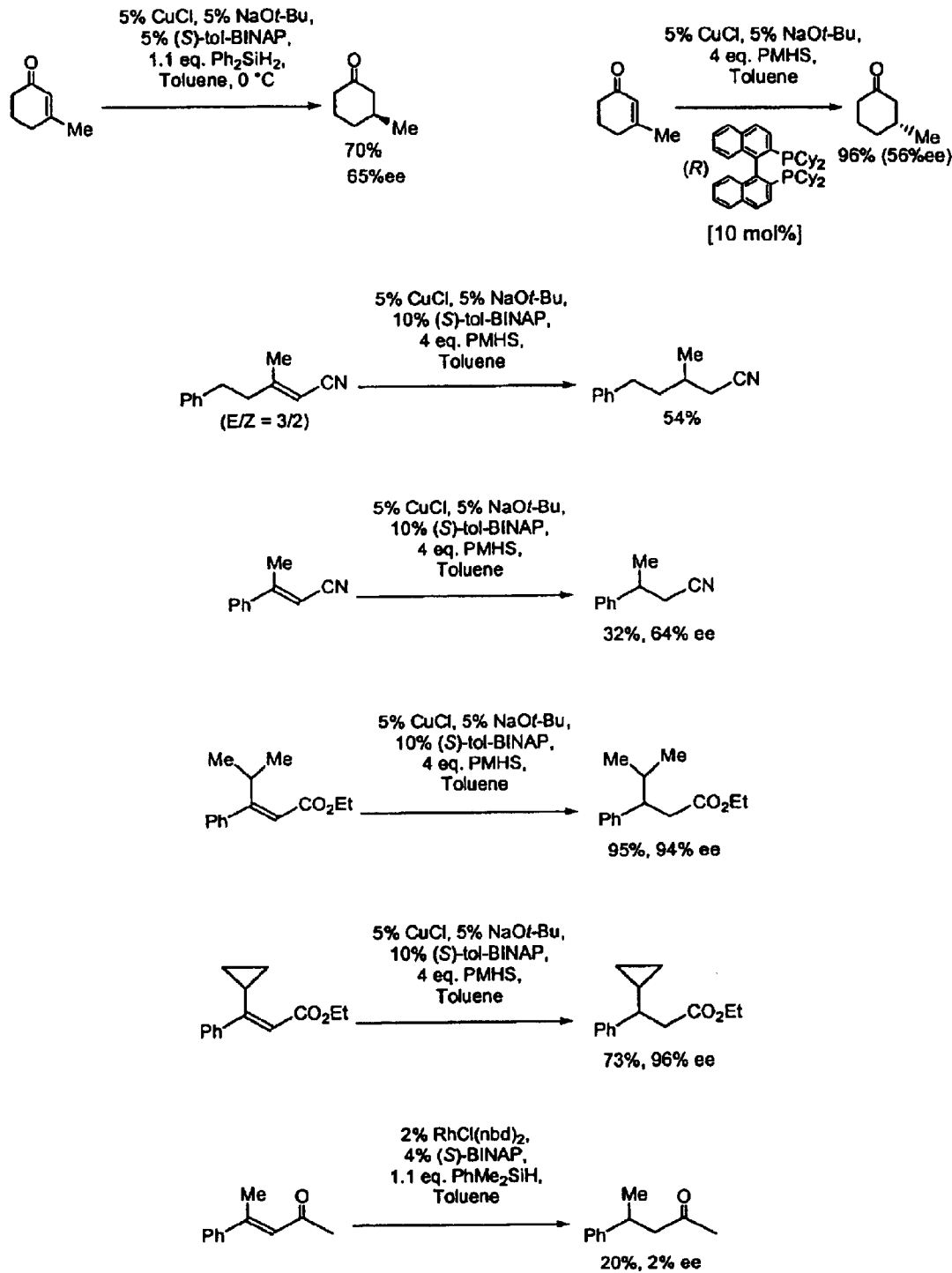
FIG. 1 depicts certain embodiments of the present invention, including asymmetric reductions of enones and acrylonitiles, and an asymmetric reduction utilizing rhodium.
Figure 2:
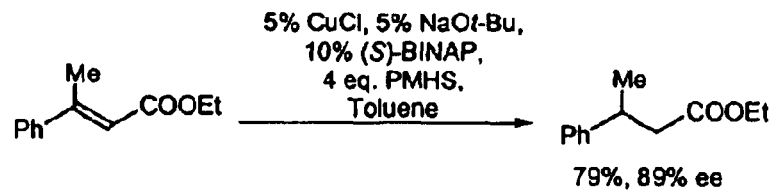
FIG. 2 depicts certain embodiments of the present invention, including asymmetric reductions of an acyclic enoate and cyclic and acyclic enones.
Figure 2:
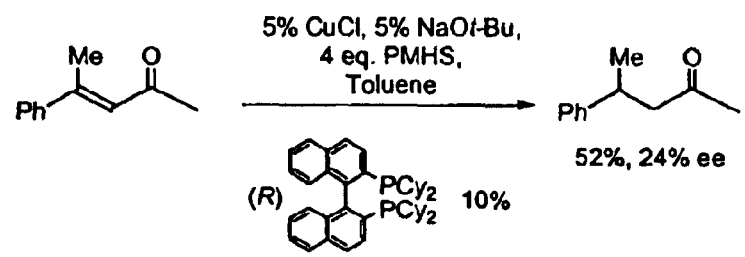
Figure 2:
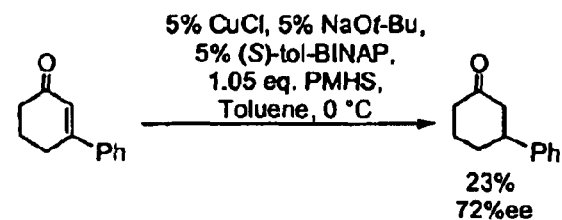
Figure 2:
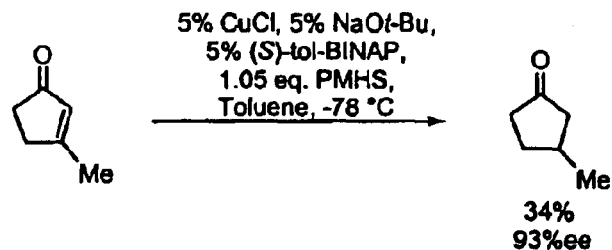
Figure 2:
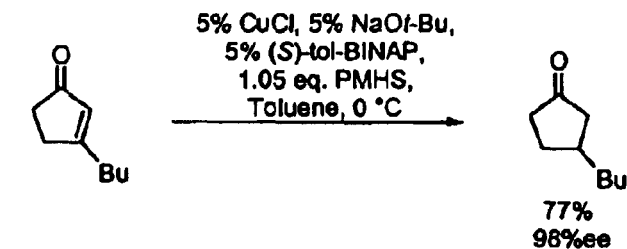
Figure 3:
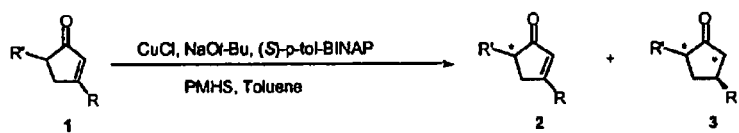
FIG. 3 depicts the results of kinetic resolutions of seven racemic 3,5-dialkylcyclopentanones performed using the procedure described in Example 21.
Figure 4:
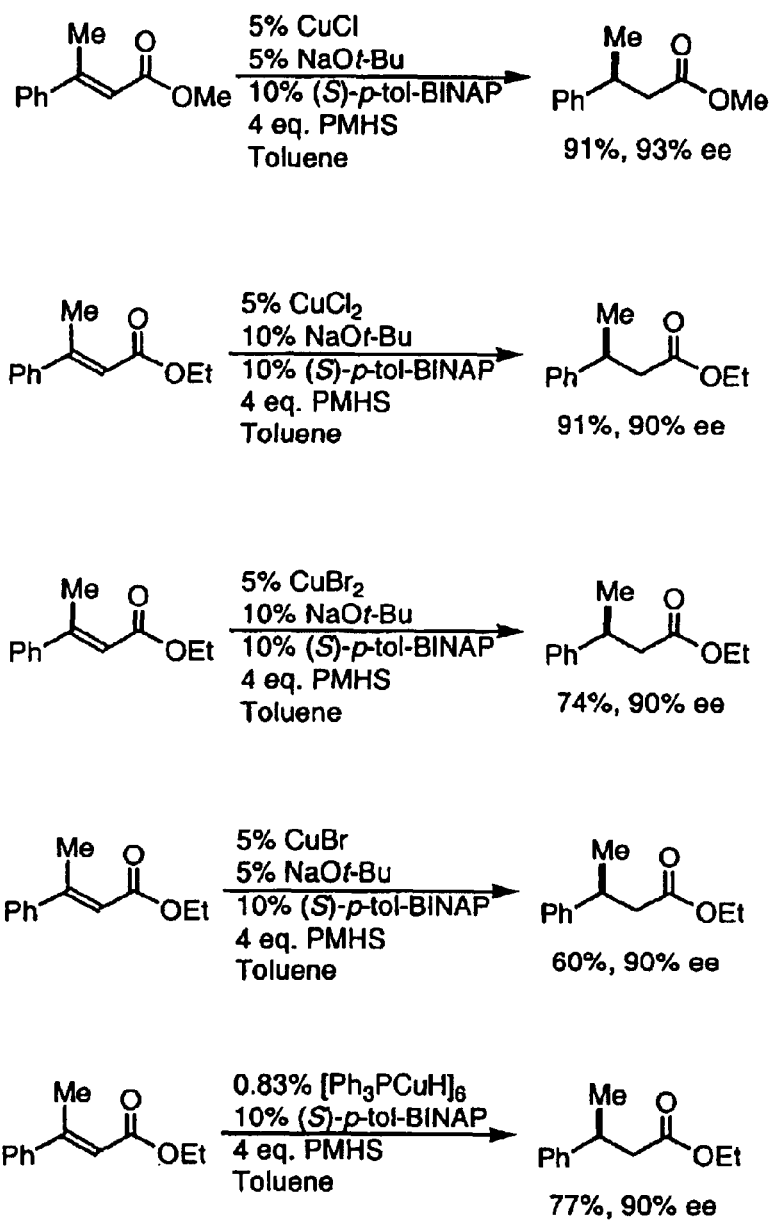
FIG. 4 depicts five examples of asymmetric 1,4-reductions of acyclic enoates, using PMHS and (S)-p-tol-BINAP.
Figure 5:
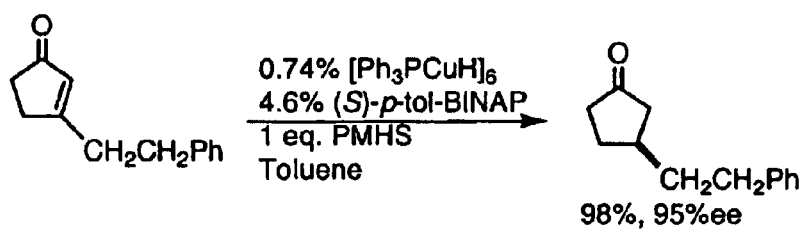
FIG. 5 depicts three examples of asymmetric 1,4-reductions of 3-phenethylcyclopentene, using various silanes, (S)-p-tol-BINAP, and no more than 1 mol % copper catalyst.
Figure 5:
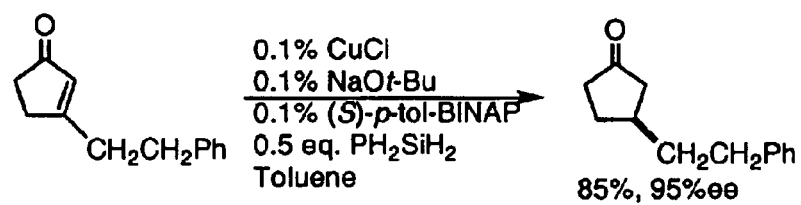
Figure 5:
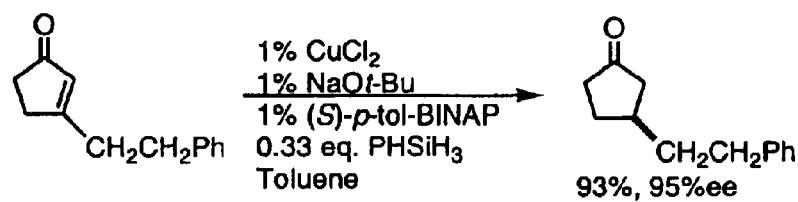

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. The advantages of enantiomerically pure compounds (reviewed in, e.g., Stinson, S. C., *Chem Eng News*, Sep. 28, 1992, pp. 46–79) include fewer side effects and greater potency in many cases. As described herein, the present invention makes available methods and reagents for asymmetric 1,4-reduction of and 1,4-addition to enoates, enones, acrylonitriles and the like. The primary constituents of the method, set out in more detail below, are: a chiral, non-racemic transition metal catalyst, consisting essentially of transition metal atom and an asymmetric ligand; an enoate, enone, acrylonitrile or the like; a base; and a hydride source, e.g., a silane, or a nucleophile, e.g., a carbanion or cyanide. Furthermore, in certain embodiments, the methods of the present invention may be practiced at or below room temperature.

Definitions

For convenience, before further description of the present invention, certain terms employed in the specification, examples, and appended claims are collected here.

The phrase "asymmetric 1,4-reduction" is art-recognized and refers to the reduction, to produce an asymmetric center, of the carbon-carbon π-bond within a conjugated pair of π-bonds, consisting of a carbon-carbon π-bond and a carbon-heteroatom π-bond. The figure below depicts a representative asymmetric 1,4-reduction reaction.

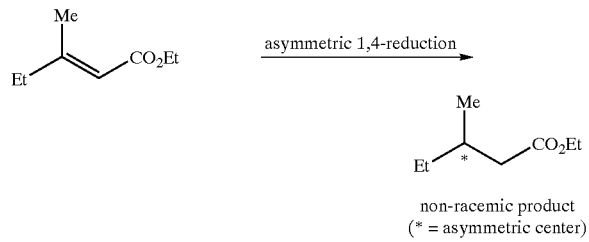

The phrase "asymmetric 1,4-addition" is art-recognized and refers to the addition of a nucleophile, to produce an asymmetric center, to the carbon-carbon π-bond within a conjugated pair of π-bonds, consisting of a carbon-carbon π-bond and a carbon-heteroatom π-bond. The figure below depicts a representative asymmetric 1,4-addition reaction.

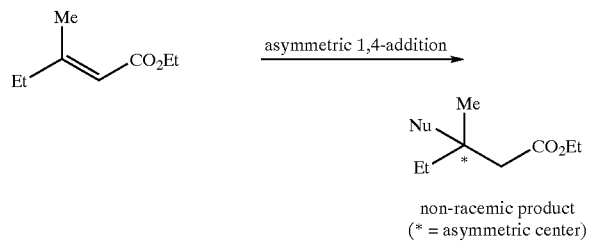

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above, or from a Lewis base. Electrophilic moieties useful in the method of the present invention include halides and sulfonates.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

$$\begin{array}{c} \% \text{ enantiomeric} \\ \text{excess } A(ee) \end{array} = (\% \text{ enantiomer } A) - (\% \text{ enantiomer } B)$$

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

The term "non-racemic" means a preparation having greater than 50% of a desired stereoisomer, more preferably at least 75%. "Substantially non-racemic" refers to preparations which have greater than 90% ee for a desired stereoisomer, more preferably greater than 95% ee.

The term "room temperature" is recognized in the art and means a comfortable indoor temperature, generally between 20 and 25 C.

The term "ligand" refers to an organic molecule comprising an unshared electron pair that is available for donation to a metal atom.

The term "bidentate ligand" refers to a ligand comprising two unshared electron pairs that are available for simultaneous donation to a metal atom.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "arylalkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that comprise a double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

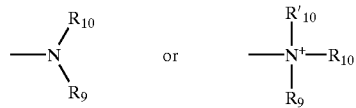

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

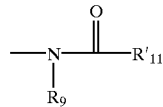

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

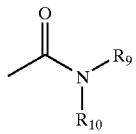

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The term "carbonyl" is art recognized and includes such moieties as can be represented by the general formula:

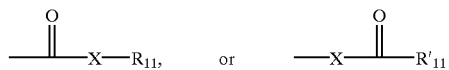

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

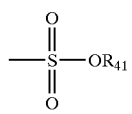

in which $R_{41}$ is an electron pair, hydrogen, alkyl, cycloalkyl, or aryl.

The term "sulfate" is art recognized and includes a moiety that can be represented by the general formula:

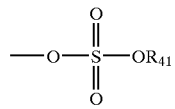

in which $R_{41}$ is as defined above.

The term "sulfonamido" is art recognized and includes a moiety that can be represented by the general formula:

in which $R_9$ and $R'_{11}$ are as defined above.

The term "sulfamoyl" is art-recognized and includes a moiety that can be represented by the general formula:

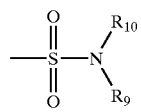

in which $R_9$ and $R_{10}$ are as defined above.

The terms "sulfoxido" or "sulfinyl", as used herein, refers to a moiety that can be represented by the general formula:

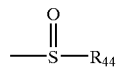

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

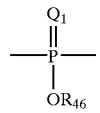

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

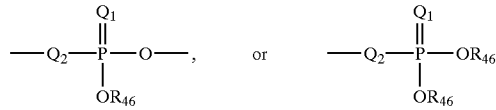

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

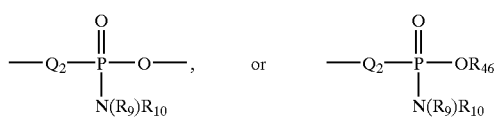

wherein $R_9$ and $R_{10}$ are as defined above, and $Q_2$ represents O, S or N.

A "phosphonamidite" can be represented in the general formula:

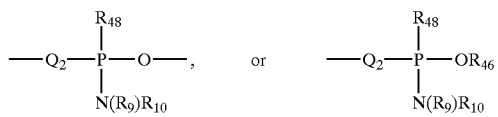

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dielectric constant ($\epsilon$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Methods of the Invention

In certain embodiments, the methods of the present invention are represented by the generalized reaction depicted in Scheme 1:

Scheme 1

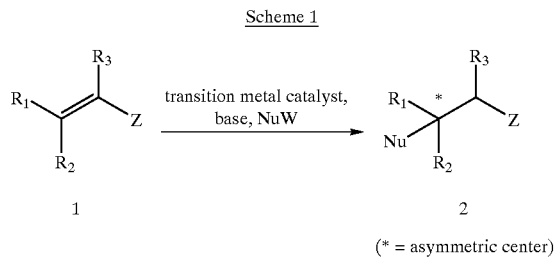

(* = asymmetric center)

wherein
    Z represents an electron withdrawing group selected from the group consisting of formyl, acyl, —CN, —C(O)OR, —C(O)N(R)$_2$, nitro, nitroso, —S(O)$_2$R, —S(O)$_2$N(R)$_2$, —C(NR)—R, —C(NOR)—R, and —C(NN(R)$_2$)—R;
    R represents independently for each occurrence hydrogen, alkyl, heteroalkyl, cycloalkyl, heterocycloalkyl, aryl, heteroaryl, aralkyl, heteroaralkyl, or —(CH$_2$)$_m$—R$_{80}$;
    R$_1$, R$_2$, and R$_3$ are independently selected from the group consisting of H, alkyl, heteroalkyl, cycloalkyl, heterocycloalkyl, aryl, heteroaryl, aralkyl, heteroaralkyl, —Si(R)$_3$, and —(CH$_2$)$_m$—R$_{80}$;

the transition metal catalyst consists essentially of a transition metal atom and an asymmetric ligand;

Nu represents hydrogen, alkyl, heteroalkyl, aryl, heteroaryl, —(CH$_2$)$_m$—R$_{80}$, —Si(R)$_3$, —Sn(R)$_3$, —CN, or —N(R)$_2$;

W represents a Group 1 cation, Group 2 cation, transition metal cation, silyl, or stannyl;

the base is selected from the set consisting of hydrides, carbonates, fluorides, phosphates, alkoxides, phenoxides, amides, carbanions, and silyl anions;

taken together, any two groups selected from Z, R$_1$, R$_2$, and R$_3$ may form a ring comprising a total of 5–7 atoms in the backbone of said ring; said ring may comprise one or two heteroatoms in its backbone; and said ring may bear instances of R;

R$_{80}$ represents independently for each occurrence aryl, cycloalkyl, cycloalkenyl, heterocyclyl, or polycyclyl;

m is an integer in the range 0 to 8 inclusive; and the carbon marked with an asterisk in compound 2 is asymmetric.

In certain embodiments, the subject method is represented by Scheme 1 and the associated definitions, wherein the transition metal catalyst consists essentially of a transition metal atom and an asymmetric bidentate ligand.

In certain embodiments, the subject method is represented by Scheme 1 and the associated definitions, wherein the transition metal catalyst consists essentially of a transition metal atom and an asymmetric bidentate bisphosphine ligand.

In certain embodiments, the subject method is represented by Scheme 1 and the associated definitions, wherein the transition metal catalyst consists essentially of a copper atom and an asymmetric ligand.

In certain embodiments, the subject method is represented by Scheme 1 and the associated definitions, wherein the transition metal catalyst consists essentially of a copper atom and an asymmetric bidentate ligand.

In certain embodiments, the subject method is represented by Scheme 1 and the associated definitions, wherein the transition metal catalyst consists essentially of a copper atom and an asymmetric bidentate bisphosphine ligand.

In certain embodiments, the subject method is represented by Scheme 1 and the associated definitions, wherein the transition metal catalyst consists essentially of a copper atom and p-tol-BINAP.

In certain embodiments, the subject method is represented by Scheme 1 and the associated definitions, wherein the base is selected from the set consisting of alkoxides, phenoxides, and amides.

In certain embodiments, the subject method is represented by Scheme 1 and the associated definitions, wherein the base is an alkoxide.

In certain embodiments, the subject method is represented by Scheme 1 and the associated definitions, wherein the base is sodium tert-butoxide.

In certain embodiments, the subject method is represented by Scheme 1 and the associated definitions, wherein NuW is a silane; and Nu is hydrogen.

In certain embodiments, the subject method is represented by Scheme 1 and the associated definitions, wherein NuW is polymethylhydrosiloxane (PMHS), phenylsilane, diphenylsilane, or dimethylphenylsilane; and Nu is hydrogen.

In certain embodiments, the subject method is represented by Scheme 1 and the associated definitions, wherein Nu is alkyl, aryl, —CN. —Si(R)$_3$, or —Sn(R)$_3$.

In certain embodiments, the subject method is represented by Scheme 1 and the associated definitions, wherein Nu is alkyl, aryl, or —CN.

In certain embodiments, the subject method is represented by Scheme 1 and the associated definitions, wherein Z is selected from the group consisting of formyl, acyl, —CN, —C(O)OR, —C(O)N(R)$_2$, nitro, nitroso, —S(O)$_2$R, and —S(O)$_2$N(R)$_2$.

In certain embodiments, the subject method is represented by Scheme 1 and the associated definitions, wherein Z is selected from the group consisting of formyl, acyl, —CN, —C(O)OR, and —C(O)N(R)$_2$.

In certain embodiments, the subject method is represented by Scheme 1 and the associated definitions, wherein Z is selected from the group consisting of acyl, —C(O)OR, and —C(O)N(R)$_2$.

In certain embodiments, the subject method is represented by Scheme 1 and the associated definitions, wherein Z is selected from the group consisting of acyl and —C(O)OR.

In certain embodiments, the subject method is represented by Scheme 1 and the associated definitions, wherein Z is —C(O)OR.

In certain embodiments, the subject method is represented by Scheme 1 and the associated definitions, wherein Z is acyl.

In certain embodiments, the subject method is represented by Scheme 1 and the associated definitions, wherein the transition metal catalyst consists essentially of a copper atom and an asymmetric bidentate bisphosphine ligand; NuW is a silane; and Nu is hydrogen.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; and Nu is hydrogen.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; and Z is selected from the group consisting of formyl, acyl, —CN, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; and Z is selected from the group consisting of acyl, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; and Z is selected from the group consisting of acyl and —C(O)OR.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; and Z is —C(O)OR.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; and Z is acyl.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and Z is selected from the group consisting of formyl, acyl, —CN, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and Z is selected from the group consisting of acyl, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and Z is selected from the group consisting of acyl and —C(O)OR.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and Z is —C(O)OR.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and Z is acyl.

In certain embodiments, the subject method is represented by Scheme I and the associated definitions, wherein the transition metal catalyst consists essentially of a copper atom and an asymmetric bidentate bisphosphine ligand; NuW is a silane; Nu is hydrogen; and the base is selected from the set consisting of alkoxides, phenoxides, and amides.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; and the base is an alkoxide.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; and the base is sodium tert-butoxide.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and the base is selected from the set consisting of alkoxides, phenoxides, and amides.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and the base is an alkoxide.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; and the base is sodium tert-butoxide.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; the base is selected from the set consisting of alkoxides, phenoxides, and amides; and Z is selected from the group consisting of formyl, acyl, —CN, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; the base is an alkoxide; and Z is selected from the group consisting of formyl, acyl, —CN, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is a silane; Nu is hydrogen; the base is sodium tert-butoxide; and Z is selected from the group consisting of formyl, acyl, —CN, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; the base is selected from the set consisting of alkoxides, phenoxides, and amides; and Z is selected from the group consisting of formyl, acyl, —CN, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; the base is an alkoxide; and Z is selected from the group consisting of formyl, acyl, —CN, —C(O)OR, and —C(O)N(R)$_2$.

In certain embodiments, the subject method is represented by Scheme 1 and the associated definitions, wherein the transition metal catalyst consists essentially of a copper atom and an asymmetric bidentate bisphosphine ligand; NuW is polymethylhydrosiloxane (PMHS), phenylsilane, diphenylsilane, or dimethylphenylsilane; Nu is hydrogen; the base is sodium tert-butoxide; and Z is selected from the group consisting of formyl, acyl, —CN, —C(O)OR, and —C(O)N(R)$_2$.

In certain embodiments, the subject method is represented by Scheme 1 and the associated definitions, wherein the solvent is a hydrocarbon.

In certain embodiments, the subject method is represented by Scheme 1 and the associated definitions, wherein the solvent is an aromatic hydrocarbon.

In certain embodiments, the subject method is represented by Scheme 1 and the associated definitions, wherein the solvent is toluene.

In certain embodiments, the subject method is represented by Scheme 1 and the associated definitions, wherein the method is conducted at or below about 50 C.

In certain embodiments, the subject method is represented by Scheme 1 and the associated definitions, wherein the method is conducted at or below room temperature.

In certain embodiments, the subject method is represented by Scheme 1 and the associated definitions, wherein the method is conducted at or below about 0 C.

In certain embodiments, the subject method is represented by Scheme 1 and the associated definitions, wherein the method is conducted at or below about −70 C.

In certain embodiments, the subject method is represented by Scheme 1 and the associated definitions, wherein the product has an enantiomeric excess greater than about 50%.

In certain embodiments, the subject method is represented by Scheme 1 and the associated definitions, wherein the product has an enantiomeric excess greater than about 70%.

In certain embodiments, the subject method is represented by Scheme 1 and the associated definitions, wherein the product has an enantiomeric excess greater than about 90%.

In certain embodiments, the subject method is represented by Scheme 1 and the associated definitions, wherein the product has an enantiomeric excess greater than about 95%.

Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants, products and catalyst.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix.

Subsequent Transformations

A product synthesized by a method of the present invention may be either an end-product or an intermediate in a synthesis scheme. In cases where the product synthesized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, and analgesics.

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system.

A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples which are included merely for purposes of illustration of certain aspects and embodiments of the present invention, and are not intended to limit the invention.

Example 1
Asymmetric Conjugate Reduction of α,β-unsaturated Esters Using a Chiral Phosphine-Copper Catalyst Highly enantioselective conjugate reductions of α,β-unsaturated esters were carried out by combining catalytic amounts of CuCl, NaOt-Bu, and (S)-p-Tol-BINAP with 4 equivalents of PMHS relative to the substrate. Reductions proceeded at room temperature to give products in high yields and with ee's of 80–92%. The absence of non-linear effects indicates that a 1:1 ratio of p-Tol-BINAP:Cu exists in the catalytic complex.

Currently, there are few catalysts that can reduce carbon-carbon double bonds to generate products with stereocenters β to carbonyls and with high enantiomeric excess (ee). In this area, asymmetric conjugate additions of nucleophiles to α,β-unsaturated ketones have been intensely investigated (Scheme 1); the best catalysts for these reactions work well for a limited number of substrates and nucleophiles.[1] In some cases, asymmetric hydrogenation catalysts also provide access to products with stereocenters β to carbonyls.[2] Asymmetric conjugate reduction of an α,β-unsaturated carbonyl portion of a molecule can also generate a stereocenter β to a carbonyl.[3] Despite the numerous catalysts available for conjugate reduction,[4] only Pfaltz's chiral semicorrin cobalt system is a highly effective catalyst for asymmetric conjugate reductions. In this system, sodium borohydride is used as the stoichiometric reducing agent.[5,6]

Scheme 1

Asymmetric Conjugate Addition:

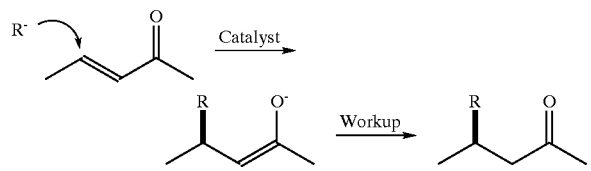

Asymmetric Hydrogenation:

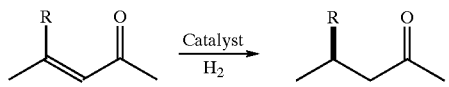

Asymmetric Conjugate Reduction:

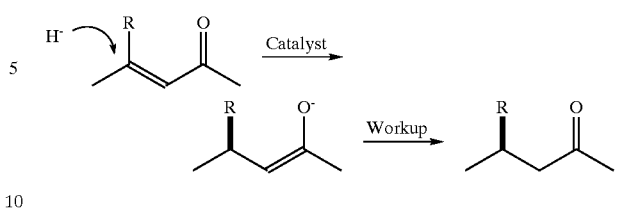

We have investigated whether a copper hydride, with a chiral phosphine ligand, can be used as a catalyst for asymmetric conjugate reduction using a silane reagent as the stoichiometric reductant. Achiral phosphine-copper hydride complexes, such as $[(Ph_3P)CuH]_6$, have been shown to act as catalysts for conjugate reductions of α,β-unsaturated carbonyl compounds in combination with phenylsilane or phenyldimethylsilane.[7,8] We now report that a catalyst formed from p-tol-BINAP,[9] CuCl, and NaOt-Bu, affects the asymmetric conjugate reduction of α,β-unsaturated esters in the presence of four equivalents of polymethylhydrosiloxane (PMHS) relative to the substrate. We felt that using PMHS, a safe and inexpensive polymer that has been previously employed as a stoichiometric reductant in metal catalyzed reductions of ketones[10] and imines,[11] would greatly enhance the utility of any process that we would develop.

In practice, we were able to generate an efficient catalyst in situ by first combining (S)-p-tol-BINAP, CuCl, and NaOt-Bu in toluene, followed by addition of PMHS. For a series of α,β-unsaturated esters, conjugate reductions usually took 24 hours at room temperature with 5 mol % catalyst and 4 equivalents of PMHS. As shown in Table 1, products were obtained with good ee's and in excellent yields. When the amount of catalyst was lowered to 1 mol %, a longer reaction time was necessary for the reaction to go to completion, but the ee of the product was unchanged. The reaction worked best when carried out under air free conditions, presumably due to the sensitivity of copper hydrides to oxygen. The asymmetric reductions of (E)- and (Z)-isomers of several substrates were examined. As shown in entries 3–8, (E)- and (Z)-isomers react to give products with nearly the same ee, but with the opposite enantiomer predominating.

TABLE 1

Asymmetric Conjugate Reductions with (S)-p-tol-BINAP, CuCl, NaOt-Bu, and PMHS[a]

| Entry | Substrate[b] | Product | Time (hr) | Yield[c] (%) | ee[d] (%) |
|---|---|---|---|---|---|
| 1 | Me / Ph / OEt | Me / Ph / OEt | 24 | 84 | 90[e] |
| 2 | Me / Cy / OEt | Me / Cy / OEt | 22 | 89 | 92 |

TABLE 1-continued

Asymmetric Conjugate Reductions with (S)-p-tol-BINAP, CuCl, NaOt-Bu, and PMHS[a]

| Entry | Substrate[b] | Product | Time (hr) | Yield[c] (%) | ee[d] (%) |
|---|---|---|---|---|---|
| 3 | Ph-C(Et)=CH-C(O)-OEt | Ph-CH(Et)-CH2-C(O)-OEt | 25 | 98 | 91 |
| 4 | Ph-C(Et)=C(C(O)O)-OEt | Ph-CH(Et)-CH2-C(O)-OEt | 27 | 98 | 83 |
| 5 | Ph-CH2CH2-C(Me)=CH-C(O)-OEt | Ph-CH2CH2-CH(Me)-CH2-C(O)-OEt | 20 | 95 | 84 |
| 6 | Ph-CH2CH2-C(Me)=C(C(O)O)-OEt | Ph-CH2CH2-CH(Me)-CH2-C(O)-OEt | 18 | 96 | 83 |
| 7 | Me2C=CH-CH2CH2-C(Me)=CH-C(O)-OEt | Me2C=CH-CH2CH2-CH(Me)-CH2-C(O)-OEt | 25 | 90 | 85[f] |
| 8 | Me2C=CH-CH2CH2-C(Me)=C(C(O)O)-OEt | Me2C=CH-CH2CH2-CH(Me)-CH2-C(O)-OEt | 23 | 93 | 80 |
| 9 | Me-(CH2)5-C(Me)=CH-C(O)-OEt | Me-(CH2)5-CH(Me)-CH2-C(O)-OEt | 24 | 94 | 81 |

[a]Reactions were run at 0.25 M [olefin], with 4 equivalents of PMHS, 5 mol % CuCl, 5 mol % NaOt-Bu, 10 mol % (S)-p-tol-BINAP, at room temperature.
[b]All substrates were either >99:1 (E) or >99:1 (Z).
[c]Yields are the average of two isolated yields of >95% purity as determined by GC, $^1$H NMR, and, for new compounds, elemental analysis.
[d]The average ee for two reactions is reported for each entry.
[e]Stereochemistry of the product was assigned by hydrolysis to the acid, and comparison to commercially available (S)-3-phenylbutyric acid.
[f]Stereochemistry of the product was assigned by comparison to ethyl (R)-citronellate prepared from commercially available (R)-citronellic acid.

The use of two equivalents of (S)-p-tol-BINAP relative to CuCl provided products with ee's that were slightly higher than when the ratio was 1:1. This result indicated that in the catalytic complex, a ratio greater than 1:1 of p-tol-BINAP: copper might be present. In order to probe this question, the reduction of ethyl trans-β-methylcinnamate (Table 1, entry 1) was performed using p-tol-BINAP of varying ee. As shown in FIG. 1, a linear correlation between the ee of the ligand and that of the product was observed, indicating that a 1:1 ratio of ligand to metal is present in the catalytic complex.[12]

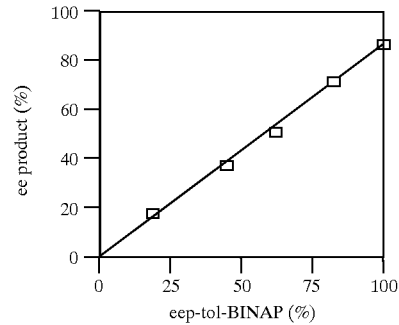

FIG. 1. Conjugate reduction of ethyl trans-β-methylcinnamate using p-tol-BINAP of varying ee. Each data point is the average of two reactions, line corresponds to a least-squares linear regression of the data with slope= 0.909, intercept=1.450, and $r^2$=0.998.

We propose that (p-tol-BINAP)CuH is the key intermediate in the catalytic cycle of the reaction that is responsible for discriminating between the enantiotopic faces of the alkene (Scheme 2). Upon combining p-tol-BINAP, CuCl, and NaOt-Bu, formation of (p-tol-BINAP)CuOt-Bu most likely occurs.[13] Addition of PMHS then results in a σ-bond metathesis between (p-tol-BINAP)CuOt-Bu and PMHS,[14] to generate (p-tol-BINAP)CuH. Asymmetric conjugate reduction then occurs, resulting in formation of a copper enolate intermediate[15] that subsequently undergoes σ-bond metathesis with PMHS to make a silylketene acetal and regenerate the copper hydride. While we have no clear rationale for the enantioselectivity of the reduction at the present time, the catalyst seems to discriminate between enantiotopic faces of the alkene based primarily on the orientation of the ester, since (E)- and (Z)-isomers give products of almost the same ee, but enriched in opposite enantiomers.

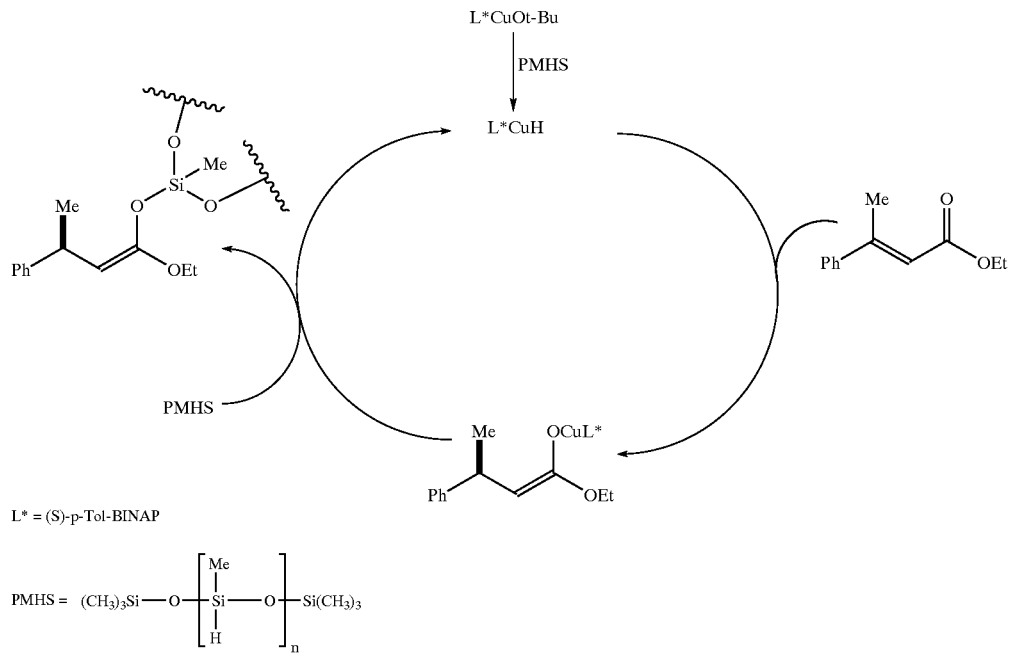

In conclusion, the combination of catalytic CuCl, NaOt-Bu, and (S)-p-Tol-BINAP with PMHS generates a highly enantioselective catalyst system for the asymmetric conjugate reduction of α,β-unsaturated esters. The advantages of this catalyst system are the commercial availability of the ligand, and the safety and low cost of PHMS. Complexes of BINAP and copper have previously found application in asymmetric aldol reactions[16] and kinetic resolutions of chiral esters.[17] The results of this study indicate that similar complexes will be useful for asymmetric reductions. Further work to examine the scope and mechanism of this catalyst system is in progress.

REFERENCES & NOTES FOR EXAMPLE 1

1. a) Gomez-Bengoa, E.; Heron, N. M.; Didiuk, M. T.; Luchaco, C. A.; Hoveyda, A. H. *J. Am. Chem. Soc.* 1998, 120, 7649. b) Keller, E.; Maurer, J.; Naasz, R.; Schader, T.; Meetsma, A.; Feringa, B. L. *Tetrahedron: Asymmetry* 1998 9, 2409. c) Nakagawa, Y.; Kanai, M.; Nagaoka, Y.; Tomioka, K. *Tetrahedron*, 1998, 54, 10295. d) Takaya, Y.; Ogasawara, M.; Hayashi, T.; Sakai, M.; Miyaura, N. *J. Am. Chem. Soc.* 1998, 120, 5579. e) Yan, M.; Yang, L.-W.; Wong, K.-Y.; Chan, A. S. C. *J. Chem. Soc., Chem. Commun.* 1999, 11. f) Krause, N. *Angew. Chem. Int. Ed.* 1998, 37, 283, and references sited within.

2. a) Asymmetric hydrogenations that generate a chiral center β to a carbonyl: 1) Yamamoto, K.; Ikeda, K.; Yin, L. K. *J. Organomet. Chem.* 1989, 370, 319. 2) Saburi, M.; Takeuchi, H.; Ogasawara, M.; Tsukahara, T.; Ishii, Y.; Ikariya, T.; Takahashi, T.; Uchida, Y. *J. Organomet. Chem.* 1992, 428, 155. 3) Uemura, T.; Zhang, X.; Matsumura, K.; Sayo, N.; Kumobayashi, H.; Ohta, T.; Nozaki, K.; Takaya, H. *J. Org. Chem.* 1996, 61, 5510. 4) Yamada, I.; Ohkouchi, M.; Yamaguchi, M.; Yamagishi, T. *J. Chem. Soc., Perkin Trans.* 1 1997, 1869. 5) Lightfoot, A.; Schnider, P.; Pfaltz, A. *Angew. Chem. Int. Ed.* 1998, 37, 2897. b) Asymmetric hydrogenations that simutaneously generate chiral centers α and β to a carbonyl: 1) Hayashi, T.; Kawamura, N.; Ito, Y. *J. Am. Chem. Soc.* 1987, 109, 7876. 2) Burk, M. J.; Gross, M. F.; Martinez, J. P. *J. Am. Chem. Soc.* 1995, 117, 9375. 3) Sawamura, M.; Kuwano, R.; Ito, Y. *J. Am. Chem. Soc.* 1995, 117, 9602. 4) Imamoto, T.; Watanabe, J.; Wada, Y.; Masuda, H.; Yamada, H.; Tsuruta, H.; Matsukawa, S.; Yamaguchi, K. *J. Am. Chem. Soc.* 1998, 120, 1635.

3. Hayashi, T.; Yamamoto, K.; Kumada, M. *Tetrahedron Lett.* 1975, 3.

4. a) Cu Catalysts: 1) Semmelhack, M. F.; Stauffer, R. D.; Yamashita, A. *J. Org. Chem.* 1977, 42, 3180. 2) Tsuda, T.; Yoshida, T.; Kawamoto, T.; Saegusa, T. *J. Org. Chem.* 1987, 52, 1624. 3) Ito, H.; Ishizuka, T.; Arimoto, K.; Miura, K.; Hosomi, A. *Tetrahedron Lett.* 1997, 38, 8887. b) Ir Catalyst: Apple, D.C.; Brady, K. A.; Chance, J. M.; Heard, N. E.; Nile, T. A. *J. Mol. Catal.* 1985, 29, 55. c)

Mo Catalysts: 1) Keinan, E.; Perez, D. *J. Org. Chem.* 1987, 52, 2576. 2) Schmidt, T. *Tetrahedron Lett.* 1994, 35, 3513. d) Ni Catalysts: 1) Caporusso, A. M.; Giacomelli, G.; Lardicci, L. *J. Org. Chem.* 1982, 47, 4640. 2) Boudjouk, P.; Choi, S.,-B.; Hauck, B. J.; Rajkumar, A. B. *Tetrahedron Lett.* 1998, 39, 3951. e) Pd Catalysts: 1) Keinan, E.; Greenspoon, N. *J. Am. Chem. Soc.* 1986, 108, 7314. 2) Arcadi, A.; Bemocchi, E.; Cacchi, S.; Marinelli, F. *Synlett* 1991, 27. f) Pt Catalysts: 1) Barlow, A. P.; Boag, N. M.; Stone, F. G. A. *J. Organomet. Chem.* 1980, 191, 39. 2) Johnson, C. R.; Raheja, R. K. *J. Org. Chem.* 1994, 59, 2287. g) Rh Catalysts: 1) Yoshii, E.; Kobayashi, Y.; Koizumi, T.; Oribe, T. *Chem. Pharm. Bull.* 1974, 22, 2767. 2) Ojima, I.; Kogure, T. *Organometallics* 1982, 1, 1390. 3) Evans, D. A.; Fu, G. C. *J. Org. Chem.* 1990, 55, 5679. 4) Ojima, I.; Donovan, R. J.; Clos, N. *Organometallics* 1991, 10, 2606. 5) Zheng, G. Z.; Chan, T. H. *Organometallics* 1995, 14, 70.
5. a) Leutenegger, U.; Madin, A.; Pfaltz, A. *Angew. Chem. Int. Ed.* 1989, 28, 60. b) von Matt, P.; Pfaltz, A. *Tetrahedron: Asymmetry*, 1991, 2, 691. c) Misun, M.; Pfaltz, A. *Helv. Chim. Acta.* 1996, 79, 961.
6. For a recent example of a chiral aldiminato cobalt catalyst for asymmetric reduction of α,β-unsaturated amides, see: Yamada, T.; Ohtsuka, Y.; Ikeno, T. *Chem. Lett.* 1998, 1129.
7. a) Lipshutz, B. H.; Keith, J.; Papa, P.; Vivian, R. *Tetrahedron Lett.* 1998, 39, 4627. b) Mori, A.; Fujita, A.; Kajiro, H.; Nishihara, Y.; Hiyama, T. *Tetrahedron* 1999, 55, 4573.
8. [(Ph$_3$P)CuH]$_6$ also functions as a catalyst for conjugate reduction in the presence of H$_2$: Mahoney, W. S.; Stryker, J. M. *J. Am. Chem. Soc.* 1989, 111, 8818.
9. p-tol-BINAP is an abbreviation for 2,2'-Bis(di-p-tolylphosphino)-1,1'-binaphthyl, each enantiomer is commercially available.
10. a) Carter, M. B.; Schiøtt, B.; Gutiérrez, A.; Buchwald, S. L. *J. Am. Chem. Soc.* 1994, 116, 11667. b) Yun, J.; Buchwald, S. L. *J. Am. Chem. Soc.* 1999, 121, 5640. c) Mimoun, H.; de Saint Laumer, J. Y.; Giannini, L.; Scopelliti, R.; Floriani, C. *J. Am. Chem. Soc.* 1999, 121, 6158.
11. a) Verdaguer, X.; Lange, U. E. W.; Buchwald, S. L. *Angew. Chem. Int. Ed.* 1998, 37, 1103. b) Hansen, M. C.; Buchwald, S. L. *Tetrahedron Lett.* 1999, 40, 2033.
12. For a discussion of nonlinear effects, see: Girard, C.; Kagan, H. B. *Angew. Chem. Int. Ed.* 1998, 37, 2922.
13. Brestensky, D. M.; Huseland, D. E.; McGettigan, C.; Stryker, J. M. *Tetrahedron Lett.* 1988, 29, 3749.
14. Lorenz, C.; Schubert, U. *Chem. Ber.* 1995, 128, 1267.
15. Copper enolates have been observed as intermediates in BINAP-copper catalyzed asymmetric aldol reactions: Pagenkopf, B. L.; Krüger, J.; Stojanovic, A.; Carreira, E. M. *Angew. Chem. Int. Ed.* 1998, 37, 3124.
16. Krüger, J.; Carreira, E. M. *J. Am. Chem. Soc.* 1998, 120, 837.
17. Yoshizumi, T.; Takaya, H. *Tetrahedron: Asymmetry* 1995, 6, 1253.

Example 2
General Procedure for the Synthesis of α,β-unsaturated Esters

Triethylphosphonoacetate (3.97 ml, 20.0 mmol) was added to a flame-dried flask and dissolved in THF (10 ml). Sodium hydride (0.50 g, 20.8 mmol) was weighed out in a glovebox, and added to the solution of triethylphosphonoacetate. The resulting solution was stirred at room temperature for 0.5 h. Ketone (20.0 mmol) was added to a separate flame-dried flask and dissolved in THF (10 ml). The ketone solution was added via cannula to the reaction solution. The resulting solution was stirred at room temperature for the time specified. The THF was removed in vacuo, and diethyl ether and aqueous NaHCO$_3$ were added. The aqueous phase was separated and extracted 3×with diethyl ether. The combined organic phases were dried over MgSO$_4$, filtered, and concentrated in vacuo. The resulting products were mixtures of (E)- and (Z)-isomers that were separated by flash column chromatography.

Example 3
Synthesis of Ethyl 3-cyclohexylbut-2-enoate

Following the procedure outlined in Example 2, cyclohexylmethyl ketone (2.76 ml, 20.0 mmol) was converted in 18 h to the title compound as a mixture of isomers. Purification by flash column chromatography (40:1 hexanes:diethyl ether) afforded the (E)-isomer (R$_f$=0.19) as a clear oil (1.71 g, 44%). $^1$H NMR (500 MHz, CDCl$_3$): δ 5.65 (s, 1H), 4.14 (q, J=7.5 Hz, 2H), 2.14 (s, 3H), 1.99–1.95 (m, 1H), 1.81–1.68 (m, 5H), 1.30–1.14 (m, 8H). $^{13}$C NMR (125 MHz, CDCl$_3$): δ 167.6, 165.2, 114.1, 59.7, 48.9, 31.5, 26.6, 26.3, 17.6, 14.6. IR (neat): 2927, 2856, 1713, 1642, 1449, 1370, 1223, 1146, 1046, 854 cm$^{-1}$. Anal. calcd for C$_{12}$H$_{20}$O$_2$: C, 73.43; H, 10.27. Found: C, 73.22; H, 10.28. The (Z)-isomer could not be completely isolated from the (E)-isomer. The (E)-isomer was assigned by a nuclear Overhauser enhancement (NOE) study: irradiation of the methyl hydrogens at δ2.14 gave a 0% enhancement of the olefin hydrogen. Based on this observation, the stereochemistry of the isomer was assigned as shown:

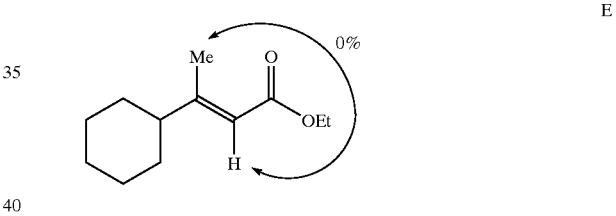

Example 4
Synthesis of Ethyl 3-phenylpent-2-enoate

Following the procedure outlined in Example 2, propiophenone (2.66 ml, 20.0 mmol) was converted in 20 h to the title compound as a mixture of isomers. Purification by flash column chromatography (20:1 hexanes:diethyl ether) afforded the (E)-isomer (R$_f$=0.29) as a yellow oil (1.99 g, 49%) and the (Z)-isomer (R$_f$=0.13) as a clear oil (1.17 g, 29%). Data for (E)-isomer: $^1$H NMR (500 MHz, CDCl$_3$): δ 7.45–7.36 (m, 5H), 6.01 (s, 1H), 4.21 (q, J=7.0 Hz, 2H), 3.11 (q, J=7.5 Hz, 2H), 1.32 (t, J=7.0 Hz, 3H), 1.08 (t, J=7.5 Hz, 3H). $^{13}$C NMR (125 MHz, CDCl$_3$): δ 166.7, 162.3, 141.3, 129.0, 128.7, 126.9, 117.0, 60.0, 24.5, 14.5, 13.8. IR (neat): 2977, 2937, 1711, 1625, 1465, 1445, 1368, 1349, 1289, 1239, 1156, 1104, 1044, 874, 769, 696 cm$^{-1}$. Anal. calcd for C$_{13}$H$_{16}$O$_2$: C, 76.44; H, 7.90. Found: C, 76.17; H, 7.94. Data for (Z)-isomer: $^1$H NMR (500 MHz, CDCl$_3$): δ 7.36–7.14 (m, 5H), 5.87 (s, 1H), 3.98 (q, J=7.0 Hz, 2H), 2.46 (q, J=7.5 Hz, 2H), 1.07 (t, J=7.0 Hz, 3H), 1.06 (t, J=7.5 Hz, 3H). $^{13}$C NMR (125 MHz, CDCl$_3$): δ 166.4, 161.3, 140.7, 128.0, 127.7, 127.2, 116.5, 60.0, 33.6, 14.2, 12.3. IR (neat): 2975, 2937, 1725, 1708, 1638, 1463, 1443, 1370, 1273, 1223, 1158, 1063, 872.1, 769, 698 cm$^{-1}$.

The (E)- and (Z)-isomers were assigned by an NOE study: for the (Z)-isomer, irradiation of the methylene hydrogens at δ 2.46 gave a 4% enhancement of the olefin hydrogen. For the (E)-isomer, irradiation of the methylene hydrogens at δ 3.11 gave a 0% enhancement of the olefin hydrogen. Based on these observations, the relative stereochemistry of the isomers was assigned as shown:

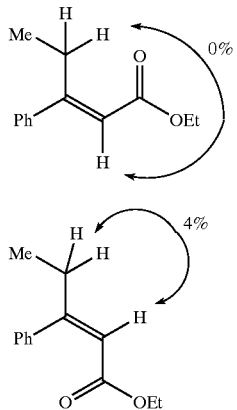

Example 5

Synthesis of Ethyl 3-methyl-5-phenylpent-2-enoate

Following the procedure outlined in Example 2, benzylacetone (3.00 ml, 20.0 mmol) was converted in 18 h to the title compound as a mixture of isomers. Purification by flash column chromatography (20:1 hexanes:diethyl ether) affored the (E)-isomer ($R_f$=0.26) as a clear oil (2.89 g, 66%) and the (Z)-isomer ($R_f$=0.34) as a clear oil (0.80 g, 18%). Data for (E)-isomer: $^1$H NMR (500 MHz, CDCl$_3$): δ 7.29–7.15 (m, 5H), 5.68 (s, 1H), 4.13 (q, J=7.5 Hz, 2H), 2.76 (t, J=8.0 Hz, 2H), 2.42 (t, J=8.0 Hz, 2H), 2.20 (s, 3H), 1.26 (t, J=7.5 Hz, 3H). $^{13}$C NMR (125 MHz, CDCl$_3$): δ 166.8, 159.0, 141.2, 128.6, 128.4, 126.2, 116.1, 59.6, 42.8, 34.0, 19.0, 14.4. IR (neat): 2981, 2939, 1713, 1648, 1495, 1455, 1368, 1273, 1221, 1140, 1096, 1050, 858, 746, 698 cm$^{-1}$. Anal. calcd for C$_{14}$H$_{18}$O$_2$: C, 77.03; H, 8.31. Found: C, 76.95; H, 8.39. Data for (Z)-isomer: $^1$H NMR (500 MHz, CDCl$_3$): δ 7.29–7.17 (m, 5H), 5.69 (s, 1H), 4.14 (q, J=7.5 Hz, 2H), 2.91 (t, J=8.0 Hz, 2H), 2.78 (t, J=8.0 Hz, 2H), 1.87 (s, 3H), 1.27 (t, J=7.5 Hz, 3H). $^{13}$C NMR (125 MHz, CDCl$_3$): δ 166.4, 159.7, 141.8, 128.6, 128.5, 126.1, 116.8, 59.7, 35.7, 34.7, 25.7, 14.5. IR (neat): 2979, 2937, 1710, 1648, 1495, 1455, 1376, 1229, 1162, 1136, 1052, 862, 748, 698 cm$^{-1}$.

The (E)- and (Z)-isomers were assigned by an NOE study: for the (Z)-isomer, irradiation of the methyl hydrogens at δ 1.87 gave a 5% enhancement of the olefin hydrogen. For the (E)-isomer, irradiation of the methyl hydrogens at δ 2.20 gave a 1% enhancement of the olefin hydrogen. Based on these observations, the relative stereochemistry of the isomers was assigned as shown:

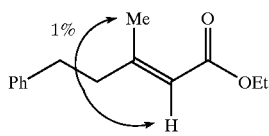

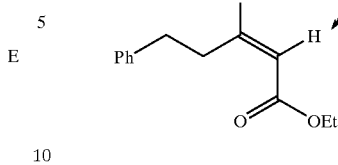

Example 6

Isolation of Isomerically Pure (E)- and (Z)-Ethyl Geranate

Ethyl geranate was purchased as a mixture of (E)- and (Z)-isomers. The isomers were separated by flash column chromatography (20:1 hexanes:diethyl ether). Data for (E)-isomer: $^1$H NMR (500 MHz, CDCl$_3$): δ 5.67 (s, 1H), 5.08 (m, 1H), 4.14 (q, J=7.5 Hz, 2H), 2.16–2.15 (m, 7H), 1.69 (s, 3H), 1.61 (s, 3H), 1.28 (t, J=7.5 Hz, 3H). Data for (Z)-isomer: $^1$H NMR (500 MHz, CDCl$_3$): δ 5.65 (s, 1H), 5.15 (t, J=7.0 Hz, 1H), 4.14 (q, J=7.5 Hz, 2H), 2.63 (t, J=7.5 Hz, 2H), 2.16 (q, J=7.5 Hz, 2H), 1.89 (s, 3H), 1.68 (s, 3H), 1.62 (s, 3H), 1.27 (t, J=7.5 Hz, 3H). The (E)- and (Z)-isomers were assigned by comparison to published data for each isomer. See Inoue, S.; Takaya, H.; Tani, K.; Otsuka, S.; Sato, T.; Noyori, R. *J. Am. Chem. Soc.* 1990, 112, 4897.

Example 7

Synthesis of Ethyl 3-methylnon-2-enoate

Following the procedure outlined in Example 2,2-octanone (3.13 ml, 20.0 mmol) was converted in 22 h to the title compound as a mixture of isomers. Purification by flash column chromatography (30:1 hexanes:diethyl ether) afforded the (E)-isomer ($R_f$=0.14) as a clear oil (1.45 g, 37%). $^1$H NMR (500 MHz, CDCl$_3$): δ 5.66 (s, 1H), 4.14 (q, J=7.0 Hz, 2H), 2.15 (s, 3H), 2.13 (t, J=7.5 Hz, 3H), 1.31–1.26 (m, 10H), 0.89 (t, J=7.0 Hz, 3H). $^{13}$C NMR (125 MHz, CDCl$_3$): δ 167.2, 160.7, 115.6, 59.7, 41.2, 31.9, 29.1, 27.6, 22.8, 18.9, 14.6, 14.3. IR (neat): 2931, 2860, 1717, 1648, 1461, 1382, 1368, 1349, 1219, 1144, 1113, 1044, 862, 725 cm$^{-1}$. Anal. calcd for C$_{12}$H$_{22}$O$_2$: C, 72.68; H, 11.18. Found: C, 72.84; H, 11.27. The spectroscopic characteristics of the synthetic material were consistent with previously reported data for the (E)-isomer. See Genard, S.; Patin, H. *Bull. Soc. Chim. Fr.* 1991, 128, 397.

Example 8

General Procedure for the Asymmetric Conjugate Reduction of α,β-unsaturated Esters (S)-p-tol-BINAP (110 mg, 0.162 mmol) was placed into a flame-dried Schlenk flask, and dissolved in toluene (6 mL). The solution was degassed by briefly opening the solution to vacuum, then backfilling with argon (this degassing procedure was repeated 3 additional times). The Schlenk flask was moved into an argon-filled glovebox. NaOt-Bu (8 mg, 0.081 mmol) and CuCl (8 mg, 0.081 mmol) were placed into a vial, and dissolved in the reaction solution. The resulting solution was stirred 10–20 min. The Schlenk flask was removed from the glovebox, PMHS (0.36 mL, 6 mmol) was added to the reaction solution under argon purge. The resulting solution turned a reddish orange color. The α,β-unsaturated ester (1.5 mmol) was added to the reaction solution under argon purge and the resulting solution was stirred for the indicated time. Consumption of the α,β-unsaturated ester was monitored by GC. When the reaction was complete, the Schlenk flask was opened and ethanol (0.3 mL) was added dropwise to the reaction (CAUTION! Rapid addition of ethanol caused extensive bubbling and foaming of the solution). The result-

Example 9
Synthesis of Ethyl (S)-3-phenylbutyrate

Following the procedure outlined in Example 8, ethyl trans-β-methylcinnamate (0.275 mL, 1.5 mmol) was converted in 24 h to the title compound. Purification by flash column chromatography (30:1 hexanes:ethyl acetate) afforded the pure product as a clear oil (0.245 g, 85% yield). Chiral HPLC analysis (Chiracel OB column) determined that the product had an ee of 90%. $^1$H NMR (500 MHz, CDCl$_3$): δ 7.31–7.18 (m, 5H), 4.07 (q, J=7.0 Hz, 2H), 3.28 (m, 1H), 2.61 (dd, J=15.0, 7.0 Hz, 1H), 2.53 (dd, J=15.0, 8.0 Hz, 1H), 1.30 (d, J=7.0 Hz, 3H), 1.18 (t, J=7.0 Hz, 3H). $^{13}$C NMR (125 MHz, CDCl$_3$): δ 172.6, 145.9, 128.7, 127.0, 126.6, 60.5, 43.2, 36.7, 22.0, 14.4. IR (neat): 2970, 1733, 1495, 1453, 1370, 1268, 1163, 1084, 1028, 762, 698 cm$^{-1}$. $[α]^{25°\ C.}$+19° (c 1.1, CHCl$_3$). Anal. calcd for C$_{12}$H$_{16}$O$_2$: C, 74.97; H, 8.39. Found: C, 75.19; H, 8.55.

Example 10
Synthesis of Ethyl 3-cyclohexylbutyrate

Following the procedure outlined in Example 8, ethyl (E)-3-cyclohexylbut-2-enoate (0.294 g, 1.5 mmol) was converted in 22 h to the title compound. Purification by flash column chromatography (20:1 hexanes:ethyl ether) afforded the pure product as a clear oil (0.274 g, 92% yield). $^1$H NMR (300 MHz, CDCl$_3$): δ 4.13 (q, J=7.0 Hz, 2H), 2.36 (dd, J=14.5, 5.0 Hz, 1H), 2.07 (dd, J=14.5, 9.0 Hz, 1H), 1.90–1.61 (m, 6H), 1.29–0.88 (m, 12H); $^{13}$C NMR (125 MHz, CDCl$_3$): δ 174.0, 60.2, 42.8, 39.5, 35.6, 30.5, 29.1, 26.9, 26.8, 26.7, 16.6, 14.5. IR (neat): 2925, 2854, 1737, 1449, 1370, 1310, 1279, 1252, 1171, 1096, 1034, 891 cm$^{-1}$. $[α]^{25°\ C.}$−2.3° (c 1.3, CHCl$_3$). Anal. calcd for C$_{12}$H$_{22}$O$_2$: C, 72.68; H, 11.18. Found: C, 72.67; H, 11.06.

The ee was determined by first reducing the product with LiAlH$_4$ to the alcohol, followed by reaction with trifluoroacetic anhydride. The enantiomers of the resulting trifluoroacetate were separated by chiral GC. Chiral GC analysis of the trifluoroacetate (Chiraldex G-TA column) determined that the product had an ee of 92%.

Example 11
Synthesis of Ethyl 3-phenylpentanoate

Following the procedure outlined in Example 8, ethyl (E)-3-phenylpent-2-enoate (0.306 g, 1.5 mmol) was converted in 25 h to the title compound. Purification by flash column chromatography (20:1 hexanes:ethyl ether) afforded the pure product as a clear oil (0.300 g, 97% yield). Chiral HPLC analysis (Chiracel OB column) determined that the product had an ee of 91%. $^1$H NMR (300 MHz, CDCl$_3$): δ 7.31–7.16 (m, 5H), 4.02 (q, J=7.0 Hz, 2H), 3.00 (m, 1H), 2.59 (ABX, J$_{AB}$=15.0 Hz, J$_{AX}$=7.0 Hz, J$_{BX}$=8.0 Hz, 2H), 1.78–1.53 (m, 2H), 1.12 (t, J=7.0 Hz, 3H), 0.79 (t, J=7.0 Hz, 3H); $^{13}$C NMR (125 MHz, CDCl$_3$): δ 172.7, 144.0, 128.5, 127.7, 126.5, 60.3, 44.1, 41.7, 29.3, 14.3, 12.1. IR (neat): 2967, 2933, 1733, 1603, 1495, 1372, 1331, 1248, 1162, 1096, 1032, 953, 758, 700 cm$^{-1}$. $[α]^{25°\ C.}$+18° (c 1.1, CHCl$_3$). Spectroscopic data was consistent with previously reported data for this compound. See Katritzky, A. R.; Feng, D.; Lang, H. J. Org. Chem. 1997, 62, 706.

Example 12
Synthesis of Ethyl 3-phenylpentanoate

Following the procedure outlined in Example 8, ethyl (Z)-3-phenylpent-2-enoate (0.306 g, 1.5 mmol) was converted in 27 h to the title compound. Purification by flash column chromatography (20:1 hexanes:ethyl ether) afforded the pure product as a clear oil (0.303 g, 98% yield). Chiral HPLC analysis (Chiracel OB column) determined that the product had an ee of 83%. $^1$H NMR data was the same as reported for the previous example. $[α]^{25°\ C.}$−17° (c 1.4, CHCl$_3$).

Example 13
Synthesis of Ethyl 3-Methyl-5-phenylpentanoate

Following the procedure outlined in Example 8, ethyl (E)-3-methyl-5-phenylpent-2-enoate (0.327 g, 1.5 mmol) was converted in 20 h to the title compound. Purification by flash column chromatography (30:1 hexanes:ethyl acetate) afforded the pure product as a clear oil (0.319 g, 97% yield). Chiral HPLC analysis (Chiracel OB column) determined that the product had an ee of 84%. $^1$H NMR (300 MHz, CDCl$_3$): δ 7.30–7.15 (m, 5H), 4.12 (q, J=7.0 Hz, 2H), 2.62 (m, 2H), 2.35 (dd, J=15.0, 6.0 Hz, 1H), 2.16 (dd, J=15.0, 8.0 Hz, 1H), 2.02 (m, 1H), 1.73–1.45 (m, 2H), 1.25 (t, J=7.0 Hz, 3H), 1.01 (d, J=7.0 Hz, 3H). $^{13}$C NMR (125 MHz, CDCl$_3$): δ 173.3, 142.6, 128.5, 128.4, 125.9, 60.4, 42.0, 38.8, 33.5, 30.3, 19.8, 14.5. IR (neat): 2960, 2933, 1733, 1603, 1497, 1455, 1372, 1250, 1196, 1152, 1092, 1032, 746, 698. $[α]^{25°}_{c.}$+12° (c 1.0, CHCl$_3$). Spectroscopic data was consistent with previously reported data for this compound. See Misun, M.; Pfaltz, A. Helv. Chim. Acta. 1996, 79, 961.

Example 14
Synthesis of Ethyl 3-Methyl-5-phenylpentanoate

Following the procedure outlined in Example 8, ethyl (Z)-3-methyl-5-phenylpent-2-enoate (0.327 g, 1.5 mmol) was converted in 18 h to the title compound. Purification by flash column chromatography (30:1 hexanes:ethyl acetate) afforded the pure product as a clear oil (0.316 g, 96% yield). Chiral HPLC analysis (Chiracel OB column) determined that the product had an ee of 85%. $^1$H NMR data was the same as reported for the previous example. $[α]^{25°\ C.}$−17° (c 1.2, CHCl$_3$).

Example 15
Synthesis of Ethyl (R)-citronellate

Following the procedure outlined in Example 8, ethyl (E)-geranate (0.294 g, 1.5 mmol) was converted in 25 h to the title compound. Purification by flash column chromatography (20:1 hexanes:ethyl ether) afforded the pure product as a clear oil (0.255 g, 86% yield). Chiral GC analysis (Chiraldex G-TA column) determined that the product had an ee of 86%. $^1$H NMR (300 MHz, CDCl$_3$): δ 5.09 (m, 1H), 4.13 (q, J=7.0 Hz, 2H), 2.20 (dd, J=14.5, 6.0 Hz, 1H), 2.14–1.96 (m, 4H), 1.68 (s, 3H), 1.60 (s, 3H), 1.41–1.16 (m, 5H), 0.95 (d, J=6.0 Hz, 3H). $^{13}$C NMR (125 MHz, CDCl$_3$): δ 173.4, 131.6, 124.5, 60.2, 42.0, 36.9, 30.2, 25.8, 25.6, 19.7, 17.8, 14.4. IR (neat): 2966, 2916, 1737, 1449, 1376, 1289, 1189, 1152, 1081, 1034 cm$^{-1}$. $[α]^{25°\ C.}$+4.6° (c 1.3, CHCl$_3$). Anal. calcd for C$_{12}$H$_{22}$O$_2$: C, 72.68; H, 11.18. Found: C, 72.78; H, 11.05.

Example 16
Synthesis of Ethyl (S)-citronellate

Following the procedure outlined in Example 8, ethyl (Z)-geranate (0.294 g, 1.5 mmol) was converted in 23 h to the title compound. Purification by flash column chroma-tography (20:1 hexanes:ethyl ether) afforded the pure product as a clear oil (0.278 g, 94% yield). Chiral GC analysis (Chiraldex G-TA column) determined that the product had an ee of 80%. $^1$H NMR data was the same as reported for the previous example. $[\alpha]_{25°}^{C}$-3.4° (c 1.5, CHCl$_3$).

Example 17

Synthesis of Ethyl 3-methylnonanoate

Following the procedure outlined in Example 8, ethyl (E)-3-methylnon-2-enoate (0.297 g, 1.5 mmol) was converted in 24 h to the title compound. Purification by flash column chromatography (20:1 hexanes:ethyl ether) afforded the pure product as a clear oil (0.283 g, 94% yield). Chiral GC analysis (Chiraldex G-TA column) determined that the product had an ee of 81%. $^1$H NMR (300 MHz, CDCl$_3$): δ 4.13 (q, J=7.0 Hz, 2H), 2.29 (dd, J=14.5, 6.0 Hz, 1H), 2.09 (dd, J=14.5, 8.0 Hz, 1H), 1.95 (m, 1H), 1.28–1.23 (m, 13H), 0.93 (d, J=7.0 Hz, 3H), 0.88 (t, J=7.0 Hz, 3H). $^{13}$C NMR (125 MHz, CDCl$_3$): δ 173.5, 60.2, 42.1, 36.9, 32.0, 30.5, 29.6, 27.0, 22.8, 19.9, 14.4, 14.2. IR (neat): 2958, 2927, 2857, 1737, 1461, 1372, 1289, 1248, 1167, 1127, 1032 cm$^{-1}$. $[\alpha]_{25°}^{C}$+3.4° (c 1.2, CHCl$_3$). Anal. calcd for C$_{12}$H$_{24}$O$_2$: C, 71.95; H, 12.08. Found: C, 72.13; H, 11.98.

Example 18

Synthesis of β-Alkyl Cyclopentanones in High Enantiomeric Excess via Copper-Catalyzed Asymmetric Conjugate Reduction Highly enantioselective conjugate reductions of α,β-unsaturated ketones were carried out by combining catalytic amounts of CuCl, NaOt-Bu, and a chiral bis-phosphine ((S)-p-Tol-BINAP, (S)-BINAP, or (S)-BIPHEMP) with 1.05 equivalents, relative to the substrate, of polymethylhydrosiloxane (PMHS). Reductions of α-substituted αβ-unsaturated cyclopentenones proceeded to give the products in high yields and excellent ee's (92–98%). The asymmetric reductions of α-substituted α,β-unsaturated cyclohexenones and a cycloheptenone were highly enantioselective, but competing 1,2-reduction also occurred to a minor extent.

Most synthetic routes to chiral β-substituted cyclic ketones are based on the conjugate addition of nucleophiles to cyclic α,β-unsaturated ketones (Scheme 1a).[1] Recently, excellent catalysts for the asymmetric conjugate addition of nucleophiles to cyclic enones that contain a 6 or 7 membered ring have been discovered.[2] Highly enantioselective catalysts for conjugate addition of aryl, vinyl,[3] or enolate[4] nucleophiles to cyclopentenone are also known. However, catalysts for the asymmetric conjugate addition of nucleophilic alkyl groups to cyclopentenone typically afford products with enantiomeric excesses (ee's) lower than 90%.[2] Currently, the most enantioselective catalytic method to produce β-alkylcyclopentanones utilizes Rh(Me-DUPHOS) and Rh(BINAP) complexes to catalyze the asymmetric intramolecular hydroacylation of 4-substituted pent-4-enals.[5] We felt that a procedure based on asymmetric reduction of β-substituted enones, which can be readily synthesized via the Stork-Danheiser procedure,[6] could also provide a useful synthetic route to enantiomerically enriched β-substituted cyclic ketones (Scheme 1b).

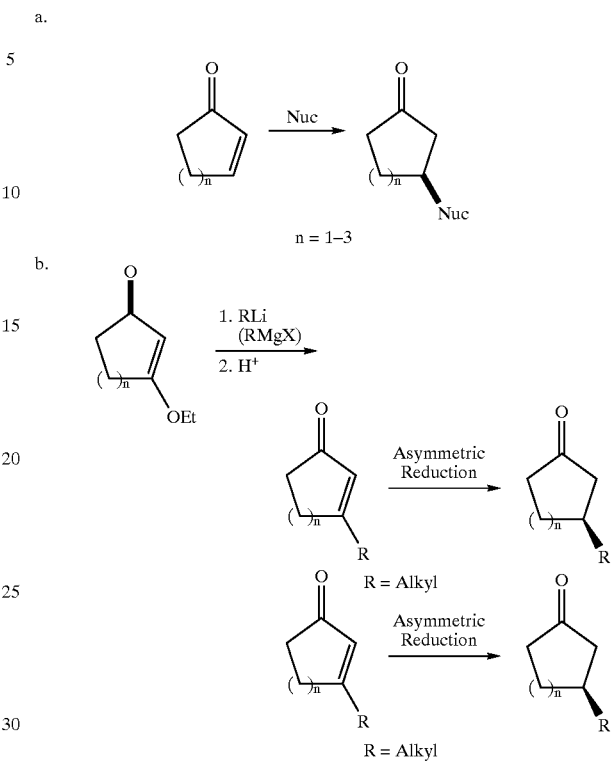

Scheme 1

Recently, we described a new copper catalyst for the asymmetric conjugate reduction of α,β-unsaturated esters.[7] This catalyst employs polymethylhydrosiloxane (PMHS), a safe and inexpensive polymer, as the stoichiometric reductant. Other catalysts for asymmetric conjugate reduction are based on chiral cobalt complexes and utilize stoichiometric amounts of borohydrides, such as NaBH$_4$.[8] Although the cobalt catalysts are very effective for the asymmetric conjugate reduction of α,β-unsaturated esters and amides, the same catalysts cannot be used for the asymmetric conjugate reduction of enones because reduction by the borohydride is rapid and non-selective. The pioneering work of Stryker, Lipshutz, and Hiyama demonstrated that achiral phosphine-copper hydrides, such as [(Ph$_3$P)CuH]$_6$, preferentially reduce enones via 1,4-reduction.[9] We now report that chiral (bis-phosphine)Cu catalysts can reduce β-substituted enones to afford chiral ketones with very high ee's. These catalysts are especially effective for the asymmetric reduction of β-substituted cyclopentenones.

In practice, efficient catalysts were generated in situ by first combining a chiral bis-phosphine ((S)-p-tol-BINAP, (S)-BINAP, or (S)-BIPHEMP),[10] CuCl, and NaOt-Bu in toluene, followed by the addition of PMHS. As shown in Table 1, cyclopentanones were obtained in high yields and excellent ee's. For most of the β-substituted cyclopentenones, conjugate reductions were complete in 24 hours with 5 mol % catalyst and one equivalent, relative to the substrate, of PMHS. Lower catalyst loadings (1 mol %) could be used without any effect on the ee of the product, but the reactions took a longer time to go to completion. Previously, we reported that 4 equivalents of PMHS were necessary for the (S)-p-tol-BINAP-derived catalyst to reduce α,β-unsaturated esters.[7] However, for the reduction of α,β-unsaturated ketones it was important to limit the amount of PMHS such that one equivalent of Si—H was present relative to substrate.[11] If extra PMHS was used, then overreduction to the saturated alcohol was observed.

TABLE 1

Asymmetric Conjugate Reductions with (S)-p-tol-BINAP, CuCl, NaOt-Bu, and PMHS[a]

| Entry | Substrate[b] | Product | Temp. (°C.) | Yield[c] (%) | ee[d] (%) |
|---|---|---|---|---|---|
| 1 | (cyclopentenone with R) | (cyclopentanone with R), R = Me | −78 | 42[e] | 94 |
| 2 | | n-Bu | 0 | 84[f] | 98 |
| 3 | | CH$_2$Ph | 0 | 78 | 96 |
| 4 | | CH$_2$CH$_2$Ph | 0 | 86 | 94 |
| 5 | (cyclopentenone, (CH$_2$)$_4$-allyl) | (cyclopentanone, (CH$_2$)$_4$-allyl) | 15 | 87 | 96[g] |
| 6 | (cyclopentenone, (CH$_2$)$_n$OBn) | (cyclopentanone, (CH$_2$)$_n$OBn) | 0 | 91 | 94 |
| 7 | (cyclopentenone, CH$_2$CH$_2$CO$_2$Me) | (cyclopentanone, CH$_2$CH$_2$CO$_2$Me) | 0 | 86 | 92 |
| 8 | (cyclopentenone, i-Pr) | (cyclopentanone, i-Pr) | 0 | 88[h] | 94 |
| 9 | (cyclohexenone with R) | (cyclohexanone with R), R = Me | −78 | 61[i] | 92[j] |
| 10 | | n-Bu | 0 | 82[k] | 87[j] |
| 11 | (cycloheptenone, CH$_2$CH$_2$Ph) | (cycloheptanone, CH$_2$CH$_2$Ph) | 0 | 82[l] | 96[g] |

[a]Reactions were performed at 0.5 M [enone], with 1.05 equivalent of PMHS, 5 mol % CuCl, 5 mol % NaOt-Bu, 5 mol % (S)-p-tol-BINAP, for 24 hours, at the temperature specified. Note: the reactions were set up with the aid of a nitrogen filled drybox.[12]
[b]See supporting information for details on substrate preparation.
[c]Yields are the average of two isolated yields of >95% purity as determined by GC and $^1$H NMR.
[d]The average ee for two reactions is reported for each entry. The absolute stereochemistry of the products in entries 1, 2, 8, 9, and 10 were assigned by comparing the sign of their optical rotations to published values (see supporting information for details). The absolute stereochemistry of all other products were assigned by analogy.
[e]Low isolated yield due to volatility of the product, GC yield was 86%.
[f]Reaction time was 12 hours.
[g](S)-BINAP was the ligand.
[h]Reaction time was 3 days. In addition to the desired product, 10% starting material was recovered.

TABLE 1-continued

Asymmetric Conjugate Reductions with (S)-p-tol-BINAP, CuCl, NaOt-Bu, and PMHS[a]

| Entry | Substrate[b] | Product | Temp. (° C.) | Yield[c] (%) | ee[d] (%) |
|---|---|---|---|---|---|

[i]Low isolated yield due to volatility of the product, GC yield was 85%.
[j](S)-BIPHEMP was the ligand.
[k]The reaction time was 2 days. In addition to the desired product, 6% of 3-butylcyclohexanol was isolated.
[l]The reaction time was 4 days. In addition to the desired product, 9% of 3-phenethylcycloheptenol was isolated.

Cyclopentenones designed to test the tolerance of the catalyst to functional groups and steric hindrance were subjected to the reduction conditions. A cyclopentenone that contained an isolated olefin was successfully reduced in high ee (entry 5). Substrates with either a benzyl ether (entry 6) or an ester (entry 7) were also reduced with high enantioselectivity. Examination of the tolerance of the catalyst to steric hindrance on the substrate revealed that longer reaction times were necessary as the steric bulk of the substituent on the β-carbon increased. For instance, the reduction of 3-isopropylcyclopentenone (entry 8) proceeded to 90% completion after 3 days to afford 3-isopropylcyclopentanone in 88% yield and 94% ee.[13,14] To date, attempted reductions of cyclopentenones with vinyl or alkynyl groups conjugated to the enone gave mixtures of products resulting from competing 1,4- and 1,6-reductions.

The conjugate reductions of β-substituted cyclohexenones and cycloheptenones produced the desired products in high ee. For cyclohexenones, the BIPHEMP-derived catalyst produced products in higher ee than the catalysts derived from the other two ligands. In some cases, minor amounts of overreduced products were isolated. For instance, the reduction of 3-methylcyclohexenone (entry 9) produced the product cleanly (92% ee), but the reduction of 3-butylcyclohexenone (entry 10) afforded the desired product (87% ee) along with 3-butylcyclohexanol (6%). Similar problems with competing overreduction were observed with the catalysts derived from p-tol-BINAP and BINAP. For 3-phenethylcycloheptenone, BINAP was the ligand of choice, and the desired product was obtained in 96% ee (entry 11). Competing 1,2-reduction of the substrate was a problem in this reduction; in addition to the desired product, 3-phenethylcycloheptenol (9%) was also isolated. The p-tol-BINAP and BIPHEMP derived catalysts produced the same mixture of the desired product and 1,2-reduced product.

Our current view is that a (bis-phosphine)CuH complex is the key intermediate in the catalytic cycle of the reduction. Conjugate reduction of cyclopentenones by such a complex should result in formation of a copper enolate that subsequently undergoes metathesis with a silane[15] to form a silyl enol ether (Scheme 2). Circumstantial evidence supporting this mechanism was obtained when the silyl bis-(enol ethers) 1–3 were isolated from the catalytic reduction of the corresponding cyclopentenones with 0.53 equivalents of diphenylsilane. Treatment of 1–3 with TBAF afforded the 3-alkylcyclopentanone with the same ee as the catalytic reduction with PMHS.

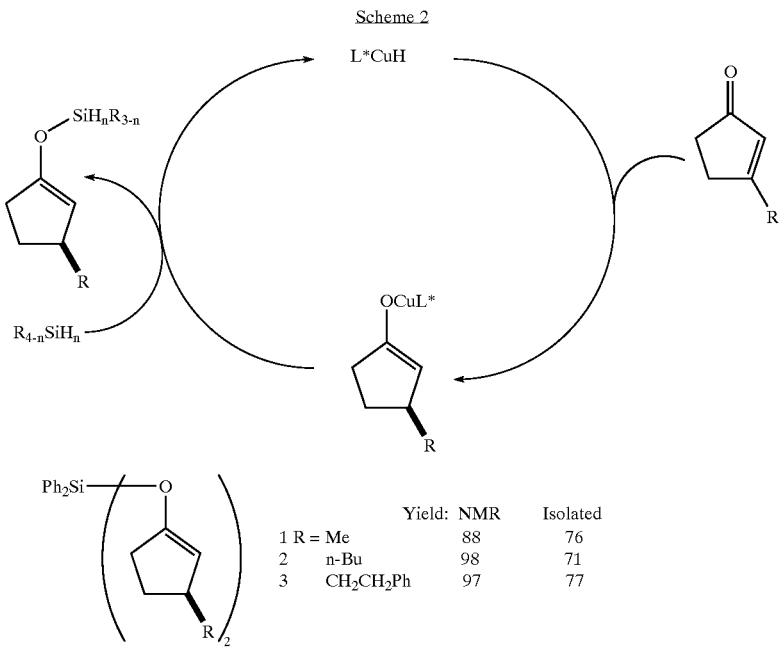

Scheme 2

| | Yield: | NMR | Isolated |
|---|---|---|---|
| 1 | R = Me | 88 | 76 |
| 2 | n-Bu | 98 | 71 |
| 3 | $CH_2CH_2Ph$ | 97 | 77 |

In conclusion, the combination of catalytic amounts of CuCl, NaOt-Bu, and a chiral bis-phosphine with PMHS generates a highly enantioselective catalyst for the asymmetric conjugate reduction of α,β-unsaturated ketones. The catalysts examined in this study produce β-substituted cyclopentanones with ee's that have not been obtained via asymmetric conjugate addition. These catalysts react with cyclopentenones exclusively via 1,4-reduction. The reductions of cyclohexenones and cycloheptenones also give the products of 1,4-reduction in high ee's, however, in these reactions competing 1,2-reduction occurs to a minor extent. Stryker and co-workers have reported that the reactivity of copper hydride complexes is highly dependent on the nature of the phosphine ligand.[16] We are currently exploring copper hydride complexes with new ligands in order to access catalysts with increased selectivity for asymmetric conjugate reduction of a wide variety of substrates.

REFERENCES & NOTES FOR EXAMPLE 18

1. For Reviews of Conjugate Addition, see: Rossiter, B. E.; Swingle, N. M. *Chem. Rev.* 1992, 92, 771. Tomioka, K.; Nagaoka, Y. Conjugate Addition of Organometallic Reagents. In *Comprehensive Asymmetric Catalysis*; Jacobsen, E. N., Pfaltz, A., Yamamoto, H., Eds.; Springer: Berlin, 1999; Volume 3, Chapter 31.1, pp 1105–1120. For recent examples of chiral additives for asymmetric conjugate addition, see: Kanai, M.; Nakagawa, Y.; Tomioka, K. *Tetrahedron* 1999, 55, 3831. Chong, J. M.; Shen, L.; Taylor, N.J. *J. Am. Chem. Soc.* 2000, 1822. For a recent example of a chiral auxiliary for asymmetric conjugate addition, see: Funk, R. L.; Yang, G. Tetrahedron Lett. 1999, 40, 1073.
2. a) Yamanoi, Y.; Imamoto, T. *J. Org. Chem.* 1999, 64, 2988. b) Hu, X.; Chen, H.; Zhang, X. *Angew. Chem. Int. Ed.* 1999, 38, 3518. c) Yan, M.; Chan, A. S. C. *Tetrahedron Lett.* 1999, 40, 6645. d) Arnold, L. A.; Imbos, R.; Mandoli, A.; de Vries, A. H. M.; Naasz, R.; Feringa, B. L. *Tetrahedron* 2000, 56, 2865. e) Escher, I. H.; Pfaltz, A. *Tetrahedron* 2000, 56, 2879. f) Krause, N. *Angew. Chem. Int. Ed.* 1998, 37, 283, and references sited within.
3. Takaya, Y.; Ogasawara, M.; Hayashi, T. *Tetrahedron Lett.* 1999, 40, 6957.
4. a) Kobayashi, S.; Suda, S.; Yamada, M.; Mukaiyama, T. *Chem. Lett.* 1994, 97. b) Arai, T.; Sasai, H.; Aoe, K.-I.; Okamura, K.; Date, T.; Shibasaki, M. *Angew. Chem. Int. Ed., Engl.* 1996, 35, 104.
5. a) Bardhart, R. W.; McMorran, D. A.; Bosnich, B. *Chem. Commun.* 1997, 589. b) Fujio, M.; Tanaka, M.; Wu, X.-M.; Funakoshi, K.; Sakai, K.; Suemune, H. *Chem. Lett.* 1998, 881.
6. Stork, G.; Danheiser, R. L. *J. Org. Chem.* 1973, 38, 1775.
7. Appella, D. H.; Moritani, Y.; Shintani, R.; Ferreira, E. M.; Buchwald, S. L. *J. Am. Chem. Soc.* 1999, 121, 9473.
8. a) Leutenegger, U.; Madin, A.; Pfaltz, A. *Angew. Chem. Int. Ed., Engl.* 1989, 28, 60. b) Misun, M.; Pfaltz, A. *Helv. Chim. Acta.* 1996, 79, 961. c) Yamada, T.; Ohtsuka, Y.; Ikeno, T. *Chem. Lett.* 1998, 1129.
9. a) Mahoney, W. S.; Stryker, J. M. *J. Am. Chem. Soc.* 1989, 111, 8818. b) Lipshutz, B. H.; Keith, J.; Papa, P.; Vivian, R. *Tetrahedron Lett.* 1998, 39, 4627. c) Mori, A.; Fujita, A.; Kajiro, H.; Nishihara, Y.; Hiyama, T. *Tetrahedron* 1999, 55, 4573.
10. p-tol-BINAP=2,2'-Bis(di-p-tolylphosphino)-1,1'-binaphthyl, BINAP=2,2'-Bis(diphenylphosphino)-1,1'-binaphthyl, BIPHEMP=2,2'-Bis(diphenylphosphino)-6,6'-dimethyl-1,1'-biphenyl
11. PMHS from Aldrich has an average molecular weight between 3200–17,000 g/mol, and a density of 1.006 g/mL. From these values, 0.06 mL PMHS/mmol Si—H was calculated and this value was used to determine the volume of PMHS to add to the reaction so that there was only one equivalent of Si—H relative to substrate.
12. We are in the process of developing reaction conditions that do not require a drybox by trying to replace CuCl with a copper salt that is less sensitive to air.
13. Isolation of the volatile product in high yield could only be accomplished by Kugelrohr distillation to remove toluene followed by chromatography with ether/pentane (a high vacuum pump could not be used to remove solvents without losing substantial amounts of the product)
14. Cyclopentenones with substituents larger than an isopropyl group on the β-carbon did not react with the catalyst; for instance, 3-t-butylcyclopentenone could not be reduced. Additionally, at present we are unable to reduce 2,3-disubstituted cyclopentenones.
15. Lorenz, C.; Schubert, U. *Chem. Ber.* 1995, 128, 1267.
16. Chen, J.-X.; Daeuble, J. F.; Stryker, J. M. *Tetrahedron* 2000, 56, 2789.

Example 19

Synthesis of β-Alkyl Cyclopentanones in High Enantiomeric Excess via Copper-Catalyzed Asymmetric Conjugate Reduction—Experimental Procedures General Considerations. THF, $Et_2O$, and $C_6D_6$ were distilled under argon from sodium/benzophenone ketyl. Toluene was distilled under argon from molten sodium. CuCl (99.995%) and NaOt-Bu were purchased from Aldrich and stored in a nitrogen-filled drybox. PMHS, benzyl 4-bromobutylether, 3-methylcyclopentenone, 3-methylcyclohexenone, (R)-3-methylcyclopentanone, and (R)-3-methylcyclohexanone were purchased from Aldrich, (S)- and (R)-p-tol-BINAP were purchased from Strem. (S)-BINAP was a gift from Pfizer, (S)-BIPHEMP was a gift from Hoffman-LaRoche. All other reagents were available from commercial sources and were used without further purification, unless otherwise noted. All manipulations involving air-sensitive materials were conducted in a Vacuum Atmospheres drybox under an atmosphere of nitrogen or argon. Unless stated otherwise, all reactions were conducted in flasks sealed with a rubber septum under a positive pressure of argon. Flash chromatography was performed on E. M. Science Kieselgel 60 (230–400 mesh) unless otherwise noted. Yields refer to isolated yields of compounds of greater than 95% purity as estimated by capillary GC and $^1H$ NMR. Yields reported in this section refer to a single experiment, while those reported in the tables are an average of two or more runs, so the numbers may differ slightly. All new compounds were characterized by $^1H$ NMR, $^{13}C$ NMR, and IR spectroscopy, in addition to elemental analysis (Atlantic Microlab, Inc.). Nuclear magnetic resonance (NMR) spectra were recorded on a Varian Mercury 300, or a Varian Unity 300, or a Varian Inova 500. Splitting patterns are designated as follows: s, singlet; d, doublet; dd, doublet of doublets; t, triplet; td, triplet of doublets; q, quartet; qd, quartet of doublets; m, multiplet. All $^1H$ NMR spectra are reported in δ units, parts per million (ppm) downfield from tetramethylsilane. All $^{13}C$ NMR spectra are reported in ppm relative to deuterochloroform (77.23 ppm), and all were obtained with $^1H$ decoupling. Infrared (IR) spectra were recorded on an ASi Applied Systems ReactIR 1000 (liquids were measured neat on a DiComp probe.) Melting points were measured on a MelTemp apparatus. Gas chromatography (GC) analyses were performed on a Hewlett-Packard 5890 or 6890 gas chromatograph with an FID detector using a 25 m×0.20 mm capillary column with cross-linked methyl siloxane as a stationary phase. GC-mass spectrometry (GS-MS) analyses were performed on a Hewlett-Packard G1800B gas chromatograph with an electron ionization detector using the same GC column described above. Chiral GC analyses were performed on a Hewlett-Packard 5890 gas chromatograph using a Chiraldex G-TA column (20 m×0.25 mm). Chiral HPLC analyses were performed on a Hewlett-Packard 1100 system with an HP 1100 Diode Array Detector (monitoring at 254 nm) using a Chiracel OD or OJ column (25 cm×0.46 cm). Racemic compounds analogous to the enantiomerically enriched compounds described below were prepared by reduction of the olefin substrates under hydrogen atmosphere catalyzed by Pd/C; except for 3-(5-hexenyl) cyclopentanone and 3-benzyloxybutyl-cyclopentanone which were prepared from 3-(5-hexenyl)cyclopent-2-enone and 3-benzyloxybutyl-cyclopent-2-enone, respectively, using 5% [(PPh$_3$)CuH]$_6$ with stoichiometric phenylsilane.[1] The HPLC or GC retention times of the racemic products were the same as those of the enantiomerically enriched products.

General Procedure for the Synthesis of Substrates (β-substituted-α,β-unsaturated ketones).

3-Butylcyclopentenone: n-BuLi (18.8 mL, 30 mmol, 1.6 M in hexane) was placed into a dry Schlenk flask and cooled to 0° C. 3-Ethoxycyclopentenone (2.52 g, 20.0 mmol) was added to a separate dry flask, dissolved in THF (40 ml), then added via syringe to the n-BuLi solution. The resulting solution was stirred at room temperature for 12 h. At this point, 1 M HCl (40 mL) was added gradually, the aqueous phase was separated and extracted 3× with diethyl ether. The combined organic phases were dried over MgSO$_4$, filtered, and concentrated in vacuo. Purification by flash chromatography (3:1 hexanes:ethyl acetate) afforded the product as a colorless liquid (1.76 g, 64%). Spectroscopic data were consistent with previously reported data for this compound.[2]

3-Benzylcyclopentenone: The general procedure for the preparation of substrates using 3-ethoxycyclopentenone (0.88 g, 7.0 mmol) and benzylmagnesium chloride (10 mmol, 1 M in diethyl ether) gave, after flash chromatography (2:1 hexanes:ethyl acetate) and Kugelrohr distillation (0.4 torr, 200° C.), the title compound as a white solid (0.58 g, 50%). m.p. 32–33° C. Spectroscopic data were consistent with previously reported data for this compound.[3]

3-Phenethylcyclopentenone: The general procedure for the preparation of substrates using 3-methoxycyclopentenone (1.29 g, 11.5 mmol) and phenethylmagnesium chloride (23 mmol, 1M in THF) gave, after flash chromatography (4:1 hexanes:ethyl acetate), the title compound as a colorless liquid (2.01 g, 94%). Spectroscopic data were consistent with previously reported data for this compound.[4]

3-(5-hexenyl)cyclopent-2-enone: Mg turnings (972 mg, 40 mmol) were placed into a dry Schlenk flask, then THF (20 mL) was added. 6-Bromo-1-hexene (5.3 mL, 40 mmol) was placed into a separate dry flask, dissolved in THF (20 mL), then added via syringe to the Mg solution. The resulting mixture was heated at 60° C. for 12 h, then cooled to room temperature. The solution of the Grignard reagent was then separated from remaining Mg solid by transferring the solution via syringe to another Schlenk flask. The general procedure for the preparation of substrates using 3-methoxycyclopentenone (2.24 g, 20 mmol) and the solution of the Grignard reagent described above gave, after 24 h and and flash chromatography (4:1 hexanes:ethyl acetate), the title compound as a colorless liquid (2.67 g, 81%). $^1$H NMR (300 MHz, CDCl$_3$): δ 5.95–5.92 (m, 1H), 5.79 (dddd, J=17.1, 10.2, 6.6, 6.6 Hz, 1H), 5.06–4.92 (m, 2H), 2.66–2.54 (m, 2H), 2.48–2.37 (m, 4H), 2.15–2.04 (m, 2H), 1.69–1.54 (m, 2H), 1.53–1.39 (m, 2H). $^{13}$C NMR (75 MHz, CDCl$_3$): δ 209.9, 182.9, 138.3, 129.4, 114.8, 35.4, 33.5, 33.4, 31.6, 28.6, 26.6. IR (neat): 2929, 2860, 1706, 1615, 1437, 1183, 994, 909, 839 cm$^{-1}$.

3-Benzyloxybutyl-cyclopent-2-enone: A solution of a Grignard reagent was prepared following the procedure described in the synthesis of 3-(5-hexenyl)cyclopent-2-enone, using Mg turnings (302 mg, 12 mmol), THF (11 mL), and benzyl 4-bromobutylether (2.75 g, 11.3 mmol). The general procedure for the preparation of substrates using 3-ethoxycyclopentenone (0.67 mL, 5.65 mmol), gave, after 12 h and flash chromatography (3:1, then 2:1 hexanes:ethyl acetate), the title compound as a white solid (0.662 g, 48%). m.p. 46–47° C. $^1$H NMR (300 MHz, CDCl$_3$): δ 7.34–7.25 (m, 5H), 5.94 (s, 1H), 4.50 (s, 2H), 3.49 (t, J=6.0 Hz, 2H), 2.58–2.55 (m, 2H), 2.41–2.38 (m, 3H), 1.70–1.67 (m, 4H). $^{13}$C NMR (75 MHz, CDCl$_3$): δ 210.2, 182.9, 138.6, 129.7, 128.6, 127.8 (2 peaks partially resolved), 73.3, 70.0, 35.6, 33.6, 31.8, 29.8, 24.2. IR (neat): 2941, 2853, 1710, 1613, 1451, 1366, 1185, 1119, 1000, 842, 749 cm$^{-1}$.

3-(3-oxo-cyclopent-1-enyl)-propionic acid methyl ester: This compound was synthesized according to a published procedure.[5] Spectroscopic data were consistent with previously reported data for this compound.[6]

3-Isopropylcyclopentenone: Isopropylmagnesium chloride (5 mL, 10 mmol, 2 M in diethyl ether) was placed in a dry flask and cooled to 0° C. 3-Ethoxycyclopentenone (0.88 g, 7 mmol) was added dropwise to the solution of the Grignard reagent, and the resulting mixture was stirred at room temperature for 23 h. At this point, 1 M HCl (15 mL) was added gradually, the aqueous phase was separated and extracted 3×with diethyl ether. The combined organic phases were dried over MgSO$_4$, filtered, and concentrated in vacuo. The product was purified first by Kugelrohr distillation (0.1 torr, 120° C.), then by flash chromatography (1:1 pentane:ether) to afford the product as a colorless liquid (0.171 g, 20%). Spectroscopic data were consistent with previously reported data for this compound.[7]

3-Butylcyclohexenone: The general procedure for the preparation of substrates using 3-methoxycyclohexenone (1.26 g, 10 mmol) and n-BuLi (20 mmol, 1.6 M in hexane) gave, after flash chromatography (4:1 hexanes:ethyl acetate) the title compound as a colorless liquid (1.48 g, 97%). Spectroscopic data were consistent with previously reported data for this compound.[2]

3-Phenethylcycloheptenone: 3-Ethoxycycloheptenone was synthesized following published procedures.[8] The general procedure for the preparation of substrates using 3-ethoxycycloheptenone (766 mg, 4.97 mmol) and phenethymagnesium chloride (10 mmol, 1M in THF) gave, after flash chromatography (4:1 hexanes:ethyl acetate), the title compound as a colorless liquid (0.984 g, 93%). $^1$H NMR (300 MHz, CDCl$_3$): δ 7.32–7.13 (m, 5H), 5.91 (br s, 1H), 2.79 (dd, J=10.5, 7.8 Hz, 2H), 2.64–2.39 (m, 6H), 1.86–1.70 (m, 4H). $^{13}$C NMR (75 MHz, CDCl$_3$): δ 204.0, 161.1, 140.9, 129.6, 128.5, 128.3, 126.3, 43.0, 42.4, 34.4, 33.1, 25.4, 21.5. IR (neat): 3027, 2937, 2865, 1656, 1495, 1453, 1268, 878, 747, 699 cm$^{-1}$.

General Procedures for the Asymmetric Conjugate Reduction of α,β-unsaturated Ketones (Synthesis of β-Substituted Ketones).

General Procedure A: A chiral bis-phosphine ((S)-p-tol-BINAP, (S)-BINAP, or (S)-BIPHEMP) (0.05 mmol) was placed into a flame-dried Schlenk tube and dissolved in toluene (2 mL). The Schlenk tube was moved into a nitrogen-filled drybox. In the drybox, NaOt-Bu (5 mg, 0.05 mmol) and CuCl (5 mg, 0.05 mmol) were weighed into a vial. The toluene solution of the chiral bis-phosphine was added via pipet to the vial to dissolve the solids and the resulting solution was then transferred back into the Schlenk tube. The Schlenk tube was removed from the drybox, the solution was stirred 10–20 min, and PMHS (0.063 mL, 1.05 mmol) was added to the solution under argon purge. The resulting solution turned a reddish orange color. The solution was then cooled to the specified temperature. The α,β-unsaturated ketone (1.0 mmol) was added to the reaction solution under argon purge and the resulting solution was stirred for the indicated period of time. Consumption of the α,β-unsaturated ketone was monitored by GC. When the reaction was complete, the Schlenk tube was opened and water (1 mL) was added. The resulting solution was diluted with diethyl ether, washed 1×with water, 1×with brine, and back-extracted with diethyl ether. To the combined organic extracts was added TBAF (1 mmol, 1 M in THF) and the resulting solution stirred for 3 h. The solution was then washed 1×with water, 1×with brine, back-extracted with diethyl ether and the organic layer was dried over $MgSO_4$. The solvent was then removed in vacuo and the product was purified by silica column chromatography.

General Procedure B: The same general procedure as for procedure A was followed except that the chiral bis-phosphine was dissolved in toluene (1 mL), and that the α,β-unsaturated ketone (1.0 mmol) was weighed into a flame-dried flask, dissolved in toluene (1 mL), and then added to the reaction solution via canula.

(S)-3-Methylcyclopentanone: General procedure A using (S)-p-tol-BINAP and 3-methylcyclopentenone (0.1 mL, 1.0 mmol) gave, after 24 h at −78° C., the title compound in 86% G.C. yield. Purification by flash chromatography (3:1 pentane:diethyl ether) afforded the pure product as a clear liquid (0.043 g, 44% yield). Spectroscopic data were identical with commercially available (R)-3-methylcyclopentanone. $[\alpha]_D^{25°\ C.}$-156° (c 0.91, $CHCl_3$). Commercially available (R)-3-methylcyclopentanone had $[\alpha]_D^{25°\ C.}$+143° (c 1.0, $CHCl_3$). Chiral GC analysis (Chiraldex G-TA column) indicated that the title compound was obtained in 94% ee.

(S)-3-Butylcyclopentanone: General procedure A using (S)-p-tol-BINAP and 3-butylcyclopentenone (0.138 g, 1.0 mmol) gave, after 12 h at 0° C. and flash chromatography (20:1 hexanes:ethyl acetate), the title compound as a clear oil (0.126 g, 90% yield). Spectroscopic data were consistent with previously reported data for this compound.[9] $[\alpha]_D^{25°}$ c.-157° (c 1.14, $CHCl_3$) (lit.[10] $[\alpha]_D^{25°\ C.}$-59° (c 3.30, $CHCl_3$) for 46%ee); $[\alpha]_D^{25°\ C.}$-143° (c 1.13, toluene) (lit.[9] $[\alpha]_D^{25°\ C.}$-87° (c 1.2, toluene) for 65%ee). In order to determine the ee, the product was converted to the corresponding (R,R)-2,3-dimethylethylene ketal (see procedure below), and then GC analysis (Chiraldex G-TA) of the diastereomeric ketals indicated that the title compound was obtained in 97% ee.

General Procedure for Conversion of β-Substituted Ketones to Diastereomeric (R,R)-2,3-dimethylethylene Ketals for the Determination of Their Enantiomeric Excess.[11]

3-Butylcyclopentanone (24 mg, 0.17 mmol) was dissolved in toluene (1 mL), p-toluenesulfonic acid (1 mg) and (R,R)-2,3-butanediol (0.03 mL, 0.344 mmol) were added and the resulting solution was heated at 120° C. for 30 min. The solution was cooled to room temperature, poured into water, diluted with diethyl ether, washed 1× with water, and washed 1× with brine. The organic layer was dried over $MgSO_4$, and the solvent removed in vacuo. The two diastereomeric ketals were separated by chiral GC (Chiraldex G-TA). This procedure was performed on both racemic ketones and optically enriched ketones that were obtained using the asymmetric conjugate reduction protocol. Crude yields of the ketal were 95% or greater.

3-Benzylcyclopentanone: General procedure B using (S)-p-tol-BINAP and 3-benzylcyclopentenone (0.11 g, 0.7 mmol) gave, after 24 h at 0° C. and flash chromatography (6:1 pentane:diethyl ether), the title compound as a clear liquid (0.97 g, 85% yield). Spectroscopic data were consistent with previously reported data for this compound.[12] $[\alpha]_D^{25°}$ c.-96° (c 1.3, $CHCl_3$). Chiral HPLC analysis (Chiracel OD column) indicated that the title compound was obtained in 96% ee.

3-Phenethylcyclopentanone: General procedure A using (S)-p-tol-BINAP and 3-phenethylcyclopentenone (0.186 g, 1.0 mmol) gave, after 24 h at 10° C. and flash chromatography (10:1 hexanes:ethyl acetate), the title compound as a clear oil (0.159 g, 84% yield). Spectroscopic data were consistent with previously reported data for this compound.[13] Chiral HPLC analysis (Chiracel OD column) indicated that the title compound was obtained in 97% ee.

3-(5-hexenyl)cyclopentanone: General procedure A using (S)-BINAP and 3-(5-hexenyl)cyclopent-2-enone (0.164 g, 1.0 mmol) gave, after 24 h at 15° C. and flash chromatography (10:1 hexanes:ethyl acetate), the title compound as a clear oil (0.142 g, 86% yield). Spectroscopic data were consistent with previously reported data for this compound.[14] The general procedure for the preparation and chiral GC analysis of (R,R)-2,3-dimethylethylene ketals indicated that the title compound was obtained in 95% ee.

3-Benzyloxybutyl-cyclopentanone: General procedure B using (S)-p-tol-BINAP and 3-benzyloxybutyl-cyclopent-2-enone (0.146 g, 0.6 mmol) gave, after 30 h at 0° C. and flash chromatography (1:2 pentane:diethyl ether), the title compound as a clear oil (0.139 g, 94% yield). $^1H$ NMR (300 MHz, $CDCl_3$): δ 7.37–7.23 (m, 5H), 4.50 (s, 2H), 3.47 (t, J=6.3 Hz, 2H), 2.43–2.04 (m, 5H), 1.78 (ddd, J=18.0, 9.6, 1.2 Hz, 1H), 1.70–1.56 (m, 2H), 1.56–1.34 (m, 5H). $^{13}C$ NMR (75 MHz, $CDCl_3$): δ 219.8, 138.6, 128.4, 127.7, 127.6, 73.1, 70.3, 45.4, 38.7, 37.4, 35.7, 30.0, 29.7, 24.8. IR (neat): 2934, 2860, 1741, 1455, 1405, 1363, 1158, 1100, 737, 699 $cm^{-1}$. HRMS m/z calcd for $C_{16}H_{22}O_2$ 246.1620, obsd 246.1615. $[\alpha]_D^{25°\ C.}$-89° (c 1.4, $CHCl_3$). Chiral HPLC analysis (Chiracel OD column) indicated that the title compound was obtained in 94% ee.

3-(3-oxo-cyclopentyl)-propionic acid methyl ester: General procedure B using (S)-p-tol-BINAP and 3-(3-oxo-cyclopent-1-enyl)-propionic acid methyl ester (0.084 g, 0.5 mmol) gave, after 24 h at 0° C. and flash chromatography (4:1, then 2:1 hexane:ethyl acetate), the title compound as a clear oil (0.075 g, 88% yield). Spectroscopic data were consistent with previously reported data for this compound.[15] $[\alpha]_D^{25°\ C.}$-112° (c 1.3, $CHCl_3$). Conversion of the title compound to the corresponding benzyl ester followed by chiral HPLC analysis (Chiracel OD column) indicated that the title compound was obtained in 91% ee.

(S)-3-Isopropylcyclopentanone: General procedure B using (S)-p-tol-BINAP and 3-isopropylcyclopentenone (0.11 g, 0.9 mmol) gave, after 3 d at 0° C. and Kugelrohr distillation (0.4 torr, 220° C.) followed by flash chromatography (10:1 pentane:diethyl ether), the title compound as a clear liquid (0.10 g, 89% yield). In addition to the desired product, starting material (0.011 g, 10%) was also isolated. Spectroscopic data for the title compound were consistent with previously reported data.[16] $[\alpha]_D^{25°\ C.}$-200° (c 1.6, $CHCl_3$) (lit.[16] $[\alpha]_D^{25°\ C.}$-110° (c 1.0, $CHCl_3$) for 60% ee). Chiral GC analysis (Chiraldex G-TA column) indicated that the title compound was obtained in 95% ee.

(S)-3-Methylcyclohexanone: General procedure A using (S)-BIPHEMP and 3-methylcyclohexenone (0.227 mL, 2.0 mmol) gave, after 24 h at −78° C., the title compound in 85% GC yield. Purification by flash column chromatography (10:1, 4:1, 2:1 pentane:diethyl ether) afforded the pure product as a clear oil (0.139 g, 62% yield). Spectroscopic data were consistent with commercially available (R)-3-methylcyclohexanone. $[\alpha]_D^{25° C.}$ −11° (c 1.4, CHCl$_3$). Commercially available (R)-3-methylcyclohexanone had $[\alpha]D^{25°}_{c.}$+13° (c 1.5, CHCl$_3$). The general procedure for the preparation and chiral GC analysis of (R,R)-2,3-dimethylethylene ketals indicated that the title compound was obtained in 88% ee.

(S)-3-Butylcyclohexanone: General procedure A using (S)-BIPHEMP and 3-butylcyclohexenone (0.152 g, 1.0 mmol) gave, after 2 d at 0° C. and flash chromatography (8:1 hexane:ethyl acetate), the title compound as a clear oil (0.127 g, 82% yield). In addition to the desired product, 3-butylcyclohexanol (0.009 g, 6%) was also isolated. Spectroscopic data for the title compound were consistent with previously reported data for this compound.[17] $[\alpha]_D^{25°}$ c.−17° (c 1.3, CHCl$_3$); $[\alpha]_D^{25° C.}$−10° (c 1.2, toluene) (lit.[9] $[\alpha]_D^{25° C.}$+7° (c 1.14, toluene) for 83%ee enriched in (R) enantiomer). The general procedure for the preparation and chiral GC analysis of (R,R)-2,3-dimethylethylene ketals indicated that the title compound was obtained in 87% ee.

3-Phenethylcycloheptanone: General procedure A using (S)-BINAP and 3-phenethylcycloheptenone (0.128 g, 0.6 mmol) gave, after 4 d at 0° C. and flash chromatography (4:1 hexanes:ethyl acetate), the title compound as a clear oil (0.104 g, 80% yield). In addition to the desired product, 3-phenethylcycloheptenol (0.012 g, 9%) was also isolated. Spectroscopic data of the title compound were consistent with previously reported data for this compound.[18] $[\alpha]_D^{25°}$ c.−41° (c 1.2, CHCl$_3$). Chiral HPLC analysis (Chiracel OJ column) indicated that the title compound was obtained in 94% ee.

General Procedure for the Asymmetric Conjugate Reduction of α,β-unsaturated Ketones and Isolation of bis-(silylenol Ethers).

The reaction was performed using the same procedure as in general procedure A, except that Ph$_2$SiH$_2$ was added to the reaction instead of PMHS. After stirring for the specified time at the specified temperature, the reaction was warmed to RT, and the solvent was directly removed in vacuo. The Schlenk was moved into an argon-filled dry box, and 1,4-dimethoxybenzene (5.0 mg) was added to the crude mixture. Analysis by $^1$H NMR (anhydrous C$_6$D$_6$) indicated the approximate yield of the bis-(silylenol ether) (yield calculated from integrations of the vinylic protons of the product relative to the methoxy protons of the 1,4-dimethoxybenzene). The solvent was then removed in vacuo, and the product was purified by flash chromatography (EM Science Silica gel 60, 3 cm column diameter, 8 cm silica, 2 mL fractions, Rf 0.4–0.5) eluting with 50:1 pentane:diethyl ether (NOTE: high yields could only be obtained using a new bottle of silica gel, and using dry diethyl ether).

Bis-(silylenol ether) from reduction of 3-methylcyclopentenone (1): The general procedure for the reduction and isolation of bis-(silylenol ehters) using 3-methylcyclopentenone (0.10 mL, 1.01 mmol) and Ph$_2$SiH$_2$ (0.10 mL, 0.53 mmol) gave after 4 h at −78° C. an 88% NMR yield of the title compound. Purification by flash chromatography gave the title compound as a clear oil (0.148 g, 78%). $^1$H NMR (500 MHz, C$_6$D$_6$): δ 7.87–7.84 (m, 4H), 7.15–7.12 (m, 6H), 4.99–4.98 (m, 2H), 2.58–2.55 (m, 2H), 2.44–2.36 (m, 4H), 1.90–1.83 (m, 2H), 1.30–1.17 (m, 2H), 0.86 (d, J=6.5 Hz, 6H); $^{13}$C NMR (125 MHz, C$_6$D$_6$): δ 153.2, 135.2, 132.4, 130.8, 128.1, 111.4, 36.5, 33.3, 30.5, 22.3; IR (neat): 3072, 2952, 2865, 1648, 1594, 1455, 1430, 1370, 1343, 1324, 1227, 1183, 1127, 1117, 1083, 1028 cm$^{-1}$.

Anal. calcd for C$_{24}$H$_{28}$SiO$_2$: C, 76.55; H, 7.49. Found: C, 76.60; H, 7.60.

Bis-(silylenol ether) from reduction of 3-butylcyclopentenone (2): The general procedure for the reduction and isolation of bis-(silylenol ehters) using 3-butylcyclopentenone (0.162 g, 1.17 mmol) and Ph$_2$SiH$_2$ (0.11 mL, 0.61 mmol) gave after 4 h at 0° C. a 98% NMR yield of the title compound. Purification by flash chromatography gave the title compound as a clear oil (0.188 g, 70%). $^1$H NMR (500 MHz, C$_6$D$_6$): δ 7.90–7.86 (m, 4H), 7.15–7.13 (m, 6H), 5.08–5.07 (m, 2H), 2.51–2.41 (m, 6H), 1.91–1.84 (m, 2H), 1.34–1.07 (m, 14H), 0.82 (t, J=7.0 Hz, 6H); $^{13}$C NMR δ (125 MHz, C$_6$D$_6$): 153.4, 135.2, 132.4, 130.9, 128.2, 109.9, 42.0, 37.1, 33.1, 29.9, 28.5, 23.2, 14.3; IR (neat): 3072, 2954, 2921, 2852, 1648, 1594, 1457, 1430, 1378, 1339, 1225, 1183, 1127, 1117, 1054, 1044 cm$^{-1}$. Anal. calcd for C$_{30}$H$_{40}$SiO$_2$: C, 78.21; H, 8.75. Found: C, 78.29; H, 8.78.

Bis-(silylenol ether) from reduction of 3-phenethylcyclopentenone (3): The general procedure for the reduction and isolation of bis-(silylenol ehters) using 3-phenethylcyclopentenone (0.143 g, 0.77 mmol) and Ph$_2$SiH$_2$ (0.075 mL, 0.404 mmol) gave after 2 h at 0° C. a 97% NMR yield of the title compound. Purification by flash chromatography gave the title compound as a clear oil (0.168 g, 79%). $^1$H NMR (500 MHz, C$_6$D$_6$): δ 7.89–7.86 (m, 4H), 7.15–7.11 (m, 10H), 7.06–7.03 (m, 2H), 6.99–6.97 (m, 4H), 5.07–5.06 (m, 2H), 2.50–2.34 (m, 10H), 1.87–1.80 (m, 2H), 1.52–1.41 (m, 4H), 1.32–1.26 (m, 2H); $^{13}$C NMR (125 MHz, C$_6$D$_6$): δ 153.7, 142.8, 135.2, 130.9, 128.6, 128.4, 128.2, 128.1, 125.8, 109.5, 41.5, 39.2, 34.0, 33.1, 28.3; IR (neat): 3062, 3027, 2923, 2850, 1648, 1603, 1594, 1495, 1455, 1430, 1345, 1225, 1185, 1127, 1117, 1081, 1057, 1030 cm$^{-1}$. Anal. calcd for C$_{38}$H$_{40}$SiO$_2$: C, 81.97; H, 7.24. Found: C, 82.13; H, 7.30.

REFERENCES & NOTES FOR EXAMPLE 19

1. Lipshutz, B. H.; Keith, J.; Papa, P.; Vivian, R. *Tetrahedron Lett.* 1998, 39, 4627.
2. Doris, E.; Dechoux, L.; Misokowski, C. *J. Am. Chem. Soc.* 1995, 117, 12700.
3. Collins, S.; Hong, Y.; Kataoka, M.; Nguyen, T. *J. Org. Chem.* 1990, 55, 3395.
4. Matsuyama, H.; Miyazawa, Y.; Takei, Y.; Kobayashi, M. *J. Org. Chem.* 1987, 52, 1703.
5. Kim, S.; Lee, H. P. *Tetrahedron Lett.* 1988, 29, 5413.
6. Nakayama, M.; Ohira, S.; Shinke, S.; Hayashi, S. *Agric. Biol. Chem.* 1978, 42, 2399.
7. Cohen, T.; Zhang, B.; Cherkauskas, J. P. *Tetrahedron* 1994, 50, 11569.
8. Hadjiarapoglou, L.; Klein, I.; Spitzner, D.; de Meijere, A. *Synthesis* 1996, 525.
9. Stangeland, E. L.; Sammakia, T. *Tetrahedron* 1997, 53, 16503.
10. Taura, Y.; Tanaka, M.; Wu, X.-M.; Funakoshi, K.; Sakai, K. *Tetrahedron* 1991, 47, 4879.
11. a) Hiemstra, H.; Wynberg, H. *Tetrahedron Lett.* 1977, 2183. b) Gomez-Bengoa, E.; Heron, N. M.; Didiuk, M. T.; Luchaco, C. A.; Hoveyda, A. H. *J. Am. Chem. Soc.* 1998, 120, 7649.
12. Yanagisawa, A.; Habaue, S.; Yasue, K.; Yamamoto, H. *J. Am. Chem. Soc.* 1994, 116, 6130.
13. Gadwood, R. C.; Mallick, I. M.; DeWinter, A. J. *J. Org. Chem.* 1987, 52, 774.
14. Negishi, E.-I.; Maye, J. P.; Choueiry, D. *Tetrahedron* 1995, 51, 4447.
15. Andrew, D.; Hastings, D. J.; Weedon, A. C. *J. Am. Chem. Soc.* 1994, 116, 10870.

16. Barnhart, R. W.; Wang, X.; Noheda, P.; Bergens, S. H.; Whelan, J.; Bosnich, B. *J. Am. Chem. Soc.* 1994, 116, 1821.
17. Jones, P.; Reddy, C. K.; Knochel, P. *Tetrahedron* 1998, 54, 1471.
18. Kanai, M.; Nakagawa, Y.; Tomioka, K. *Tetrahedron* 1999, 55, 3843.

Example 20

Asymmetric Reduction of a 3-Alkyl-cyclopentenone

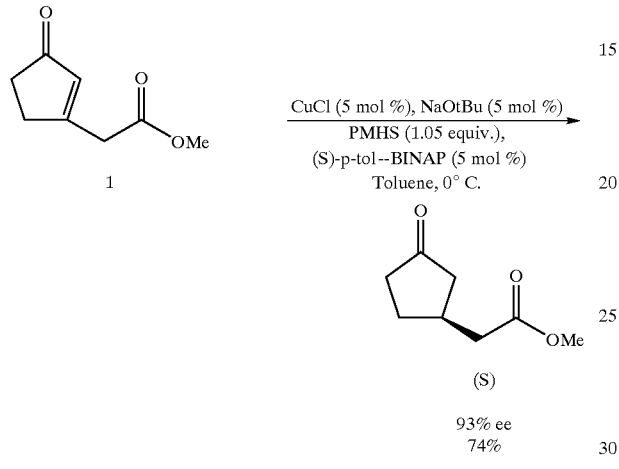

A flame dried Schlenk flask was charged with 22 mg (0.0334 mmol) of (S)-p-tol-BINAP and 0.4 mL of toluene. 3.6 mg (0.0334 mmol) of CuCl and 3.6 mg (0.0334 mmol) of NaOt-Bu were added to this solution in a drybox (N$_2$ atmosphere). Then 47 μL (0.696 mmol) of PMHS were added at room temperature and stirred for additional 20 minutes. Then cooled down to 0° C. and solution of 102 mg of substrate (1) in 0.3 mL of toluene was dropwise added at this temperature. Stirred for 24 hours at 0° C. Then diluted with diethyl ether, added water, extracted with diethyl ether. Stirred with TBAF for 3 hours at room temperature, then added water, extracted with diethyl ether, washed with brine, dried over anhydrous magnesium sulfate and concentrated. Purified by flash chromatography. Eluent: pentane/diethyl ether 3:1 to 2:1. 76 mg (74% isolated yield) of colorless oil obtained. $^1$H NMR (CDCl$_3$, 500 MHz) δ (ppm) 3.69 (s, 3H), 2.48 (m, 1H), 2.41 (m, 3H), 2.25 (m, 3H), 1.90 (m, 1H), 1.60 (m, 1H). $[\alpha]_D^{22}$=−111.9° (c 1.09, CHCl$_3$).

As depicted in the scheme below, the product of the asymmetric reduction was converted to ketal and its de (corresponding to the ee of the product) was obtained with chiral GC (Chiraldex G-TA column, 40° C., 60 min, 0.3 C/min, 130° C., 20 min, 0.7 mL/min flow rate). 93% de.

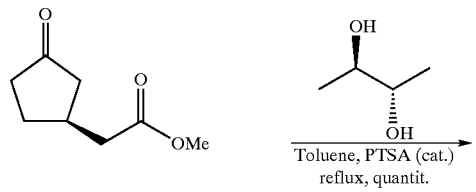

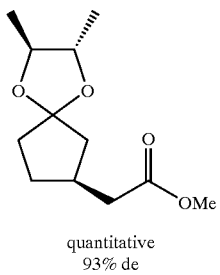

quantitative
93% de

The starting substrate (1) for this Example was prepared as depicted in the scheme below, using published protocols.[1,2]

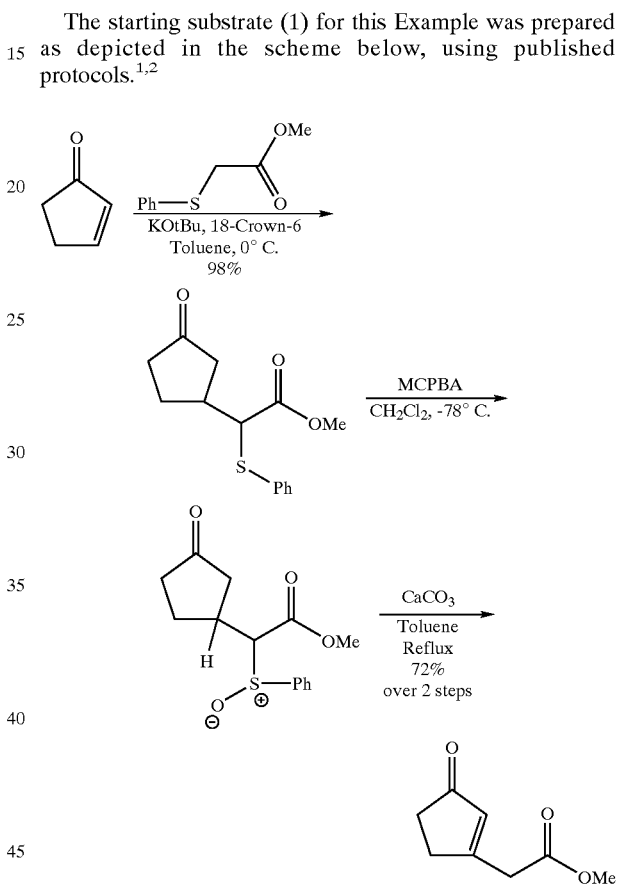

1. Takasu, M., Wakabayashi, H., Furuta, K., Yamamoto, H. *Tetrahedron Lett.,* 1988, 29, 6943.
2. Trost, B. M., Salzmann, T. N., Hiroi, K. *J. Am. Chem. Soc.,* 1976, 98, 4887.

Example 21

Kinetic Resolution of Racemic 3,5-Dialkylcyclopentenones (See Figure)

General Considerations. Toluene was passed through a column under argon atmosphere. CuCl (99.995%) and NaOt-Bu were purchased from Aldrich and stored in anitrogen filled drybox. PMHS was purchased from Aldrich and (S)-p-tol-BINAP was purchased from Strem. All other reagents were available commercially and were used without further purification, unless otherwise noted. All manipulations involving air-sensitive materials were conducted in a vacuum atmosphere drybox under the atmosphere of nitrogen or argon. Unless otherwise noted, all reactions were conducted in flasks sealed with a rubber septum under positive pressure of argon. Compounds were characterized by $^1$H NMR, $^{13}$C NMR and IR spectroscopy. Nuclear magnetic resonance (NMR) spectra were recorded on a Varian Mercury 300, or a Varian Unity 300, or a Varian Inova 500 instruments. Infrared (IR) spectra were recorded on an Asi Applied Systems ReactIR 1000 (liquids were measured neat on a DiComp probe). Flash chromatography was performed on E. M. Science Kieselgel 60 (230–400 mesh) unless otherwise noted. Gas chromatography analyses were performed on a Hewlett-Packard 6890 gas chromatograph with an FID detector using a 25 m×0.20 mm capillary column with cross-linked methyl siloxane as a stationary phase. GC-mass spectrometry (GC-MS) analyses were performed on a Hewlett-Packard G1800B gas chromatograph with an electron ionization detector using the same GC column described above. Chiral GC analyses were performed on a Hewlett-Packard 5890 gas chromatograph using a Chiraldex G-TA or B-PH (both 20 m×0.25 mm). Chiral HPLC analyses were performed on a Hewlett-Packard 1100 system with an HP Diode Array Detector (monitoring at 254 nm) using Chiracel OD, OD-H, AD columns (25 cm×0.46 cm). Racemic compounds analogous to the enantiomerically enriched compounds were prepared by reduction of the olefin substrates under hydrogen atmosphere catalyzed by Pd/C or using 5 mol % Stryker's reagent [(PPh$_3$)CuH]$_6$ in the presence of stoichiometric amount of diphenyl silane. The HPLC or GC retention times of the racemic products were the same as those of the enantiomerically enriched products. Mesitylene was purchased from Aldrich and without further purification used as an internal standard.

General procedure for the kinetic resolution of racemic 3,5-dialkyl cyclopentenones. A flame dried Schlenk flask was charged with (S)-p-tol-BINAP (5 mol %) and toluene. To this solution CuCl (5 mol %) and NaOt-Bu (5 mol %) were added in a drybox (N$_2$ atmosphere) and to the resulting light yellow solution PMHS (0.53 equiv.) was added at room temperature to give orange solution. Stirred for 20 minutes at room temperature then cooled down to the required temperature (see Kinetic Resolution Results table for reaction temperatures) and solution of substrate and mesitylene in toluene was dropwise added and stirred for 12 hours at the addition temperature. The optimal substrate's concentration is 0.1–0.4 M. The relative substrate and internal standard (mesitylene) amounts were determined by Hewlett-Packard 6890 gas chromatograph (50 to 250° C.). Reaction is quenched by addition of water and then stirring the organic phase with TBAF. Relative amounts of remaining starting material and internal standard were determined by gas chromatography and the conversion calculated. Then water added, extracted with diethyl ether, washed with brine, dried over anhydrous magnesium sulfate, and concentrated. Purified by flash chromatography. Eluent: hexane/ethyl acetate 8:1. The remaining starting was analyzed by HPLC and product was analyzed by HPLC or GC.

Kinetic resolution of 3-phenethyl-5-butyl-cyclopentenone. A flame dried Schlenk flask was charged with 8.4 mg (0.0124 mmol) of (S)-p-tol-BINAP and 0.12 mL of toluene. To this solution 1.2 mg (0.0124 mmol) of CuCl and 1.2 mg (0.0124 mmol) of NaOt-Bu were added. Then 9 µL ((0.1451 mmol) of PMHS were added at room temperature and stirred for 20 minutes. The resulting orange solution was then cooled down to –78° C. and solution of 60 mg (0.2479 mmol) of enone and 34 µL (0.2479 mmol) of mesitylene in 0.12 mL of toluene dropwise added. Stirred at this temperature. An aliquot was taken and quenched with water. GC shoed 35% conversion and HPLC (Chiracel OD, 2% isopropanol in hexane, 0.7 mL/min flow rate) gave 46% enantiomeric excess for the product. The selectivity value S was calculated using equation (1).[2] S=20 for this reaction.

$$S=\{ln[(1-c)(1-ee)]\}/\{ln[(1-c)(1+ee)]\} \tag{1}$$

The product was analyzed by HPLC (Chiracel OD-H, 1.5% isopropanol in hexane, 0.7 mL/min flow rate) and GC. 98% diastereomeric excess was obtained with 96% enantiomeric excess for the major diastereomer.

Preparation of Racemic 3,5-Dialkycyclopentanones

The racemic substrates for the kinetic resolutions described in this Example were synthesized according to published procedures (see Scheme below).[3,4,5]

Preparation of the Starting Substrates

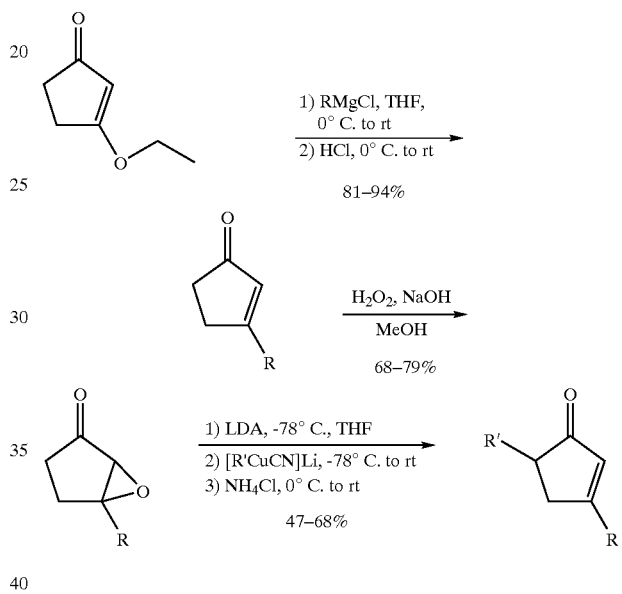

REFERENCES FOR EXAMPLE 21

1. Lipshutz, B. H.; Keith, J.; Papa, P.; Vivian, R. *Tetrahedron Lett.* 1998, 39, 4627.
2. Kagan, H. B., Fiaud, J. C. "Kinetic Resolution", *Top. Stereochem.,* 1988, 18, 249.
3. Stork, G., Danheiser, R. L. *J. Org. Chem.* 1973, 38, 1775.
4. Wasson, R. L., House, H. O. *Organic Syntheses,* 1957, Vol. 37, 58.
5. Wender, P. A., Erhardt, J. M., Letendre, L. J. *J. Am. Chem. Soc.* 1981, 103, 2114.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. The method represented by the generalized reaction depicted in Scheme 1:

Scheme 1

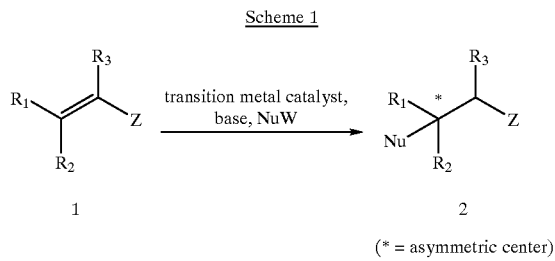

(* = asymmetric center)

wherein
- Z represents an electron withdrawing group selected from the group consisting of formyl, acyl, —CN, —C(O)OR, —C(O)N(R)$_2$, nitro, nitroso, —S(O)$_2$R, —S(O)$_2$N(R)$_2$, —C(NR)—R, —C(NOR)—R, and —C(NN(R)$_2$)—R;
- R represents independently for each occurrence hydrogen, alkyl, heteroalkyl, cycloalkyl, heterocycloalkyl, aryl, heteroaryl, aralkyl, heteroaralkyl, or —(CH$_2$)$_m$—R$_{80}$;
- R$_1$, R$_2$, and R$_3$ are independently selected from the group consisting of H, alkyl, heteroalkyl, cycloalkyl, heterocycloalkyl, aryl, heteroaryl, aralkyl, heteroaralkyl, —Si(R)$_3$, and —(CH$_2$)$_m$—R$_{80}$;
- the transition metal catalyst consists essentially of an asymmetric bidentate ligand and a copper complex selected from the group consisting of copper carboxylates, copper carbonates, copper sulfates, copper sulfonates, copper halides, copper trifluoroborates, copper phosphates and mixtures thereof;
- Nu represents hydrogen;
- NuW is a silane or polymethylhydrosiloxane (PMHS);
- the base is selected from the group consisting of alkoxides, phenoxides, and amides;
- taken together, any two groups selected from Z, R$_1$, R$_2$, and R$_3$ may form a ring comprising a total of 5–7 atoms in the backbone of said ring; said ring may comprise one or two heteroatoms in its backbone; and said ring may bear instances of R;
- R$_{80}$ represents independently for each occurrence amyl, cycloalkyl, cycloalkenyl heterocyclyl, or polycyclyl;
- m is an integer in the range 0 to 8 inclusive; and
- the carbon marked with an asterisk in compound 2 is asymmetric.

2. The method of claim 1, wherein the transition metal catalyst consists essentially of the copper complex and an asymmetric bidentate bisphosphine ligand.

3. The method of claim 1, wherein the transition metal catalyst consists essentially of the copper complex and p-tol-BINAP.

4. The method of claim 1, wherein the base is an alkoxide.

5. Tue method of claim 1, wherein the base is sodium tert-butoxide.

6. The method of claim 1, wherein NuW is polymethylhydrosiloxane (PMHS), phenylsilane, diphenylsilane, or dimethylphenylsilane.

7. The method of claim 1, wherein Z is selected from the group consisting of formyl, aryl, —CN, —C(O)OR, —C(O)N(R)$_2$, nitro, nitroso, —S(O)$_2$R, and —S(O)$_2$N(R)$_2$.

8. The method of claim 1, wherein Z is selected from the group consisting of formyl, acyl, —CN, —C(O)OR, and —C(O)N(R)$_2$.

9. The method of claim 1, wherein Z is —C(O)OR.

10. The method of claim 1, wherein Z is acyl.

11. The method of claim 1, wherein the transition metal catalyst consists essentially of the copper complex and an asymmetric bidentate bisphosphine ligand; NuW is polymethylhydrosiloxane (PMHS), phenylsilane, diphenylsilane, or dimethylphenylsilane; and Z in selected from the group consisting of formyl, acyl, —CN, —C(O)OR, and —C(O)N(R)$_2$.

12. The method of claim 1, wherein the transition metal catalyst consists essentially of the copper complex and an asymmetric bidentate bisphosphine ligand; NuW is polymethylhydrosiloxane (PMHS), phenylsilane, diphenylsilane, or dimethylphenylsilane; and Z is selected from the group consisting of acyl, —C(O)OR, and —C(O)N(R)$_2$.

13. The method of claim 1 wherein the transition metal catalyst consists essentially of the copper complex and an asymmetric bidentate bisphosphine ligand; NuW is polymethylhydrosiloxane (PMHS), phenylsilane, diphenylsilane, or dimethylphenylsilane; and Z is —C(O)OR.

14. The method of claim 1, wherein the transition metal catalyst consists essentially of the copper complex and an asymmetric bidentate bisphosphine ligand; NuW is polymethylhydrosiloxane (PMHS), phenylsilane, diphenylsilane, or dimethylphenylsilane; and Z is acyl.

15. The method of claim 1, wherein the transition metal catalyst consists essentially of the copper complex and an asymmetric bidentate bisphosphine ligand; NuW is polymethylhydrosiloxane (PMHS), phenylsilane, diphenylsilane, or dimethylphenylsilane; and the base is an alkoxide.

16. The method of claim 1, wherein the transition metal catalyst consists essentially of the copper complex and an asymmetric bidentate bisphosphine ligand; NuW is polymethylhydrosiloxane (PMHS), phenylsilane, diphenylsilane, or dimethylphenylsilane; and the base is sodium tert-butoxide.

17. The method of claim 1, wherein the transition metal catalyst consists essentially of the copper complex and an asymmetric bidentate bisphosphine ligand; the base is an alkoxide; and Z is selected from the group consisting of formyl, acyl, —CN, —C(O)OR, and —C(O)N(R)$_2$.

18. The method of claim 1, wherein the transition metal catalyst consists essentially of the copper complex and an asymmetric bidentate bisphosphine ligand; the base is sodium tert-butoxide; and Z is selected from the group consisting of formyl, acyl, —CN, —C(O)OR, and —C(O)N(R)$_2$.

19. The method of claim 1, wherein the transitional metal catalyst consists essentially of the copper complex and an asymmetric bidentate bisphosphine ligand; NuW is polymethylhydrosiloxane (PMHS), phenylsilane, diphenylsilane, or dimethylphenylsilane; the base is an alkoxide: and Z is selected from the group consisting of formyl, acyl, —CN, —C(O)OR, and —C(O)N(R)$_2$.

20. The method of claim 1, wherein the transition metal catalyst consists essentially of the copper complex and an asymmetric bidentate bisphosphine ligand; NuW is polymethylhydrosiloxane (PMHS), phenylsilane, diphenylsilane, or dimethylphenylsilane; the base is sodium tert-butoxide; and Z is selected from the group consisting of formyl, acyl, —CN, —C(O)OR and —C(O)N(R)$_z$.

* * * * *